United States Patent
Leo et al.

(10) Patent No.: US 11,413,323 B2
(45) Date of Patent: Aug. 16, 2022

(54) OPHTHALMIC COMPOSITION FOR TREATMENT OF DRY EYE DISEASE

(71) Applicant: NOVALIQ GMBH, Heidelberg (DE)

(72) Inventors: Chiara Silvana Leo, Heidelberg (DE); Sonja Krösser, Heidelberg (DE); Thomas Schlüter, Heidelberg (DE); Alice Meides, Heidelberg (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 17/228,309

(22) Filed: Apr. 12, 2021

(65) Prior Publication Data

US 2021/0236591 A1   Aug. 5, 2021

Related U.S. Application Data

(63) Continuation of application No. PCT/EP2019/077578, filed on Oct. 11, 2019.

(30) Foreign Application Priority Data

Oct. 12, 2018   (EP) .................................. 18200154
Oct. 24, 2018   (EP) .................................. 18202263
Apr. 5, 2019   (EP) .................................. 19167551

(51) Int. Cl.
| A61K 38/13 | (2006.01) |
| A61F 9/00 | (2006.01) |
| A61K 9/00 | (2006.01) |
| A61P 27/04 | (2006.01) |
| A61K 9/08 | (2006.01) |
| A61K 47/06 | (2006.01) |

(52) U.S. Cl.
CPC ............ *A61K 38/13* (2013.01); *A61F 9/0008* (2013.01); *A61K 9/0048* (2013.01); *A61P 27/04* (2018.01)

(58) Field of Classification Search
CPC ...... A61K 38/13; A61K 47/06; A61K 9/0048; A61K 9/08; A61K 31/00; A61K 47/10; A61P 27/02; A61J 1/00; A61J 1/067; A61J 1/1468
See application file for complete search history.

(56) References Cited

U.S. PATENT DOCUMENTS

| 2,616,927 A | 11/1952 | Kauck et al. |
| 4,452,818 A | 6/1984 | Haidt |
| 5,077,036 A | 12/1991 | Long, Jr. |
| 5,152,997 A | 10/1992 | Ebert et al. |
| 5,254,338 A | 10/1993 | Sakai et al. |
| 5,326,566 A | 7/1994 | Parab |
| 5,336,175 A | 8/1994 | Mames |
| 5,370,313 A | 12/1994 | Beard |
| 5,518,731 A | 5/1996 | Meadows |
| 5,667,809 A | 9/1997 | Trevino |
| 5,851,544 A | 12/1998 | Penska et al. |
| 5,874,469 A | 2/1999 | Maniar et al. |
| 5,874,481 A | 2/1999 | Weers |
| 5,904,933 A | 5/1999 | Riess et al. |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Cronelus |
| 6,140,374 A | 10/2000 | May et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,372,243 B2 | 4/2002 | Kobuch et al. |
| 6,399,087 B1 | 6/2002 | Zhang et al. |
| 6,458,376 B1 | 10/2002 | Meadows |
| 6,528,086 B2 | 3/2003 | Zhang |
| 6,730,328 B2 | 5/2004 | Maskiewicz |
| 7,001,607 B1 | 2/2006 | Menz |
| 7,026,359 B1 | 4/2006 | Gross |
| 7,258,869 B1 | 8/2007 | Berry |
| 7,740,875 B2 | 6/2010 | Dechow |
| 8,029,977 B2 | 10/2011 | Meinert et al. |
| 8,222,292 B2 | 7/2012 | Goskonda et al. |
| 8,470,873 B2 | 6/2013 | Chen |
| 8,614,178 B2* | 12/2013 | Theisinger ........... A61K 9/0048 514/1.1 |
| 8,796,340 B2 | 8/2014 | Theisinger et al. |

(Continued)

FOREIGN PATENT DOCUMENTS

| CN | 200977281 | 11/2007 |
| CN | 202136470 U | 2/2012 |

(Continued)

OTHER PUBLICATIONS

Torkildsen et al.; "A Clinical Phase 2 Study to Assess Safety, Efficacy, and Tolerability of CyclASol for the Treatment of Dry Eye Disease"; published online Nov. 16, 2017.*

Agarwal et al., "Modern Approaches to the Ocular Delivery of Cyclosporine A," Drug Discovery Today, vol. 21, No. 6, pp. 977-988, (2016); doi: 10.1016/j.drudis.2016.04.002.

Agrahari, et al., "A comprehensive insight on ocular pharmacokinetics," Drug Delivery and Translational Research, 6(6):735-754 (2016).

Ahmed, et al., "Disposition of Timolol and Inulin in the Rabbit Eye Following Corneal Versus Non-Corneal Absorption," International Journal of Pharmaceutics, 1987, 38:9-21.

Al-Amri, et al., "Long-term use of 0.003% tacrolimus suspension for treatment of vernal keratoconjunctivitis," Oman Journal of Ophthalmology, 10(3):145-149, (2017).

(Continued)

*Primary Examiner* — Jeffrey T. Palenik
(74) *Attorney, Agent, or Firm* — Hoxie & Associates LLC

(57) ABSTRACT

The invention provides ophthalmic compositions comprising about 0.1 % (w/v) cyclosporine dissolved in 1-(perfluorobutyl)pentane for use in the topical treatment of dry eye disease. The invention further provides kits comprising such compositions for the same use.

22 Claims, 6 Drawing Sheets

(56) References Cited

U.S. PATENT DOCUMENTS

| | | | |
|---|---|---|---|
| 8,916,157 | B2 | 12/2014 | Krause et al. |
| 8,986,738 | B2 | 3/2015 | Meinert |
| 9,241,900 | B2 | 1/2016 | Wilson |
| 9,308,262 | B2 | 4/2016 | Wilson |
| 9,757,459 | B2 | 9/2017 | Theisinger et al. |
| 9,757,460 | B2 | 9/2017 | Günther et al. |
| 9,770,508 | B2 | 9/2017 | Günther et al. |
| 10,045,996 | B2 | 8/2018 | Theisinger et al. |
| 10,130,707 | B2 | 11/2018 | Günther et al. |
| 2002/0004063 | A1 | 1/2002 | Zhang |
| 2002/0006442 | A1 | 1/2002 | Mishra et al. |
| 2003/0018044 | A1 | 1/2003 | Peyman |
| 2003/0027833 | A1 | 2/2003 | Cleary et al. |
| 2003/0170194 | A1 | 11/2003 | Piotrowiak |
| 2004/0044045 | A1 | 3/2004 | Burk |
| 2004/0082660 | A1 | 4/2004 | Ueno |
| 2004/0101551 | A1 | 5/2004 | Selzer |
| 2004/0265362 | A1 | 12/2004 | Susilo |
| 2004/0266702 | A1 | 12/2004 | Dawson |
| 2005/0075407 | A1 | 4/2005 | Tamarkin et al. |
| 2005/0079210 | A1 | 4/2005 | Gupta |
| 2005/0175541 | A1 | 8/2005 | Lanza et al. |
| 2005/0274744 | A1 | 12/2005 | Spada et al. |
| 2005/0288196 | A1 | 12/2005 | Horn |
| 2006/0013820 | A1 | 1/2006 | Bonnet et al. |
| 2006/0078580 | A1 | 4/2006 | Dechow |
| 2006/0153905 | A1 | 7/2006 | Carrara et al. |
| 2007/0249730 | A1 | 10/2007 | Daftary et al. |
| 2008/0019926 | A1 | 1/2008 | Krafft et al. |
| 2008/0050335 | A1 | 2/2008 | Faour et al. |
| 2008/0089923 | A1 | 4/2008 | Burkstrand et al. |
| 2008/0112895 | A1 | 5/2008 | Kottayil et al. |
| 2008/0153909 | A1 | 6/2008 | Dana et al. |
| 2008/0207537 | A1 | 8/2008 | Turner et al. |
| 2008/0234389 | A1 | 9/2008 | Mecozzi et al. |
| 2008/0254106 | A1 | 10/2008 | Bell |
| 2008/0260656 | A1 | 10/2008 | Mallard |
| 2009/0136430 | A1 | 5/2009 | Dugger |
| 2009/0149546 | A1 | 6/2009 | Chang |
| 2009/0169601 | A1 | 7/2009 | Koch et al. |
| 2010/0006600 | A1 | 1/2010 | Dascanio |
| 2010/0016814 | A1 | 1/2010 | Gokhale et al. |
| 2010/0189765 | A1 | 7/2010 | Erickson et al. |
| 2010/0210720 | A1 | 8/2010 | Pilotaz et al. |
| 2010/0226997 | A1 | 9/2010 | Bowman et al. |
| 2010/0274215 | A1 | 10/2010 | Wong et al. |
| 2011/0223208 | A1 | 9/2011 | Hill et al. |
| 2011/0269704 | A1 | 11/2011 | Seigfried |
| 2012/0010280 | A1 | 1/2012 | Aleo et al. |
| 2012/0095097 | A1 | 4/2012 | Tabuchi et al. |
| 2013/0011484 | A1 | 1/2013 | Bevier |
| 2013/0084250 | A1 | 4/2013 | Hagedorn et al. |
| 2013/0336557 | A1 | 12/2013 | Cruzat et al. |
| 2014/0004197 | A1 | 1/2014 | Theisinger et al. |
| 2014/0186350 | A1 | 7/2014 | Ghosh et al. |
| 2015/0045282 | A1 | 2/2015 | Elsohly et al. |
| 2015/0099019 | A1 | 4/2015 | Johnson |
| 2015/0224064 | A1 | 8/2015 | Günther et al. |
| 2015/0258040 | A1 | 9/2015 | Lynch et al. |
| 2016/0000941 | A1 | 1/2016 | Keller et al. |
| 2016/0159026 | A1 | 6/2016 | Günther et al. |
| 2016/0184259 | A1 | 6/2016 | Anastassov et al. |
| 2016/0243189 | A1 | 8/2016 | Gu et al. |
| 2017/0020726 | A1 | 1/2017 | Labombarbe et al. |
| 2017/0087100 | A1 | 3/2017 | Scherer et al. |
| 2017/0087101 | A1 | 3/2017 | Scherer et al. |
| 2017/0182060 | A1 | 6/2017 | Wiedersberg et al. |
| 2017/0224531 | A1 | 8/2017 | Chauhan et al. |
| 2018/0360908 | A1* | 12/2018 | Beier .................. A61K 9/0048 |
| 2019/0274970 | A1 | 9/2019 | Günther et al. |
| 2019/0321218 | A1 | 10/2019 | Graf et al. |
| 2019/0328717 | A1 | 10/2019 | Günther et al. |
| 2019/0343793 | A1 | 11/2019 | Günther et al. |
| 2020/0023035 | A1 | 1/2020 | Loscher et al. |

FOREIGN PATENT DOCUMENTS

| | | | |
|---|---|---|---|
| CN | 203524843 U | 4/2014 | |
| EP | 0 670 159 | 9/1995 | |
| EP | 1 152 749 | 11/2001 | |
| JP | S6452722 | 2/1989 | |
| JP | 2001/158734 | 6/2001 | |
| JP | 2011/006348 | 1/2011 | |
| JP | 2011/024841 | 2/2011 | |
| WO | WO 93/00991 | 1/1993 | |
| WO | WO 98/05301 | 12/1998 | |
| WO | WO 00/54588 | 9/2000 | |
| WO | WO 2010/146536 | 12/2010 | |
| WO | WO 2018/115097 | * 6/2018 | ............... A61K 9/00 |

OTHER PUBLICATIONS

Astellas Pharma US, Inc. (2019). PROGRAF(R); Highlights of Prescribing Information. Northbrook, IL: Astellas Pharma US, Inc.

Bardin et al., "Long-Range Nanometer-Scale Organization of Semifluorinated Alkane Monolayers at the Air/Water Interface," Langmuir, 2011, 27:13497-13505.

Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.

Blackie et al., "MGD: Getting to the Root Cause of Dry Eye," Review of Optometry, 2012, pp. 1-12.

Broniatowski, M. et al., "Langmuir Monolayers Characteristics of (Perfluorodecyl)-Alkanes," Journal of Physical Chemistry B, 2004, 108:13403-13411.

Chaglasian et al., "Recycling Cyclosporine," Review of Cornea & Contact Lenses, 5 pages, (2016).

Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.

Chemical Book, 5-Fluorouracil, available at <http://www.chemicalbook.com/ChemicalProductProperty_EN_CB8162744.htm>, accessed Mar. 7, 2014, 1 page.

Chhadva et al., "Meibomian Gland Disease The Role of Gland Dysfunction in Drye Eye Disease," Ophthalmology (2017) 124(11 Supplement): S20-S26.

Costa Gomes et al., "Solubility of dioxygen in seven fluorinated liquids," Journal of Fluorine Chemistry, 2004, 125:1325-1329.

Davies, "Biopharmaceutical Considerations in Topical Ocular Drug Delivery," Clin. Exper. Pharmacol. Physiol., 2000, 27:558-562.

Dias et al., "Solubility of oxygen in liquid perfluorocarbons," Fluid Phase Equilibria, 2004, 222-223:325-330.

Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).

Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.

Gayton, J., "Etiology, Prevalence, and Treatment of Dry Eye Disease," Clinical Ophthalmology, 2009, 3:405-412.

Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.

Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).

Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).

German, E.J., et al., "Reality of drop size from multi-dose eye drop bottles: is it cause for concern?" Eye, 1999, 13:93-100.

(56) References Cited

OTHER PUBLICATIONS

Hardung, H., "Semifluorierte und perfluorierte Vergindungen zur topischen und parenteralen Anwendung," 2008, 188 pages, retrieved from Internet, date accessed: Oct. 10, 2011, URL: <http://www.freidok.uni-freiburg.de/volltexte/5682/pdf/Dissertation_Hardung.pdf>.

Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

Hoerauf et al., "Combined Use of Partially Fluorinated Alkanes, Perfluorocarbon Liquids and Silicone Oil: An Experimental Study," Graefe's Archive for Clinical and Experimental Ophthalmology, 2001, 239(5):373-381.

Holm, R. et al., "A novel excipient, l-perfluorohexyloctane shows limited utility for the oral delivery of poorly water-soluble drugs," European Journal of Pharmaceutical Sciences, 2011, 42: 416-422.

International Preliminary Report on Patentability dated Apr. 13, 2021, for International Patent Application PCT/EP2019/077578, 9 Pages.

International Search Report and Written Opinion for International Application No. PCT/EP2019/077578 dated Apr. 16, 2020, 14 pages.

JPS6452722, English Machine Translation of the Abstract, Description, and Claims, Espacenet, Date Accessed: Feb. 10, 2016, 4 pages.

Kaercher et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.

Kheirkhah, A., et al., "Topical 0.005% tacrolimus eye drop for refractory vernal keratoconjunctivitis," Eye (London, England), 25(7):872-880, (2011).

Lallemand et al., "Cyclosporine A delivery to the eye: a pharmaceutical challenge," European Journal of Pharmaceutics and Biopharmaceutics, 2003, 56(3):307-318, Abstract Only (1 page).

Lemp, M., "Management of Dry Eye Disease," The American Journal of Managed Care, 2008, 14 (3):S88-S101.

Lin, H. et al., "Dry eye disease: a review of diagnostic approaches and treatments," Saudi Journal of Ophthalmology, 2014, 28:173-181.

Meinert, H. et al., "Semifluorinated Alkanes—A New Class of Compounds with Outstanding Properties for Use in Ophthalmology," European Journal of Ophthalmology, 2000, 10 (3), 189-197.

Meinert, H. et al., "The Use of Semifluorinated Alkanes in Blood-Substitutes," Biomaterials, Artificial Cells, and Immobilization Biotechnology, 1993, 21(5):583-595.

Messmer, E.M., "The Pathophysiology, Diagnosis, and Treatment of Dry Eye Disease," (2015) Deutsches Arzteblatt International, 112(5):71-82.

Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).

Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.

Moscovici, et al., "Clinical treatment of dry eye using 0.03% tacrolimus eye drops," Cornea, 31(8):945-949, (2012).

Novaliq GmbH Begins Phase II Clinical Trial of Cyclasol for the Treatment of Moderate to Severe Dry Eye Disease, (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.

Ohashi, et al., "A randomized, placebo-controlled clinical trial of tacrolimus ophthalmic suspension 0.1% in severe allergic conjunctivitis," Journal of ocular pharmacology and therapeutics, 26(2):165-174 (2010).

O'Rourke, M. et al., "Enhancing Delivery of Topical Ocular Drops," Cataract & Refractive Surgery Today Europe, 2016, 2 pages.

Perry, "Dry Eye Disease: Pathophysiology, Classification, and Diagnosis," The American Journal of Managed Care, 2008, 14(3):S79-S87.

Pflugfelder et al., "Treatment of Blepharitis: Recent Clinical Trials," 2014, 12(4):273-284, Abstract Only (2 pages).

Pflugfelder et al., "The Pathophysiology of Dry Eye Disease What We Know and Future Directions for Research," Ophthalmology (2017) 124(11 Supplement): S4-S13.

Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.

Scherer et al., "Eyesol: A Novel Topical Ocular Drug Delivery System for Poorly Soluble Drugs," Drug Development & Delivery, vol. 13, No. 1, pp. 40-44, (2013).

Schnetler et al., "Lipid composition of human meibum: a review," S Afr Optom, 2013, 72(2), 86-93.

Spöler et al., "Towards a New in vitro Model of Dry Eye: The ex vivo Eye Irritation Test," Developments in Ophthalmology, 2010, 45, 93-107.

Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.

Steven, P. et al. "Semifluorinated Alkane Eye Drops for Treatment of Dry Eye Disease—A Prospective, Multicenter Noninterventional Study" Investigative Ophthalmology & Visual Science, 2015, 56:4493, Abstract Only (1 page).

Steven et al., "Semifluorinated Alkane Eye Drops for Treatment of Dry Eye Disease Due to Meibomian Gland Disease," Journal of Ocular Pharmacology and Therapeutics, 2017, 33(9):1-8.

Tamura et al., "Tacrolimus is a class II low-solubility high-permeability drug: The effect of P-glycoprotein efflux on regional permeability of tacrolimus in rats," Journal of Pharmaceutical Sciences, 2002, 91(3):719-729 (Abstract Only), 1 page.

Tiffany, J.M., "Individual Variations in Human Meibomian Composition," Exp. Eye Res., 1978, 27, 289-300.

Wirta, David L. et al., "A Clinical Phase II Study to Assess Efficacy, Safety and Tolerability of Waterfree Cyclosporine Formulation for the Treatment of Dry Eye Disease," *Ophthalmology* 126:792-800 (2019).

Wong et al., "Perfluorocarbons and Semifluorinated Alkanes," Seminars in Ophthalmology; vol. 15 (1), 2000, p. 25-35.

Yazu, et al., "The efficacy of 0.1% tacrolimus ophthalmic suspension in the treatment of severe atopic keratoconjunctivitis," Annals of allergy, asthma & immunology, 122(4), 387-392 (2019).

\* cited by examiner

OPHTHALMIC COMPOSITION FOR TREATMENT OF DRY EYE DISEASE

CROSS-REFERENCE TO RELATED APPLICATIONS

This application is a continuation application filed under 35 U.S.C. § 111(a) of International Application No. PCT/EP2019/077578, filed on Oct. 11, 2019, which claims priority to and the benefit of European Applications Nos. 18200154.5, filed on Oct. 12, 2018, 18202263.2, filed on Oct. 24, 2018, and 19167551.1, filed on Apr. 5, 2019, the contents of each of which are hereby incorporated by reference in their entireties.

BACKGROUND OF THE INVENTION

Keratoconjunctivitis sicca, also known as dry eye disease or dysfunctional tear syndrome, is today understood as a multifunctional disorder of the tear film and of the ocular surface which results in discomfort, visual disturbance, and often even in ocular surface damage caused by tear film instability. Estimates of the prevalence of dry eye vary considerably, depending on the criteria used to define the disease, but in the U.S., it has been estimated that as many as 3.2 million women and 1.7 million men over the age of 50 have dry eye, with a projected 40% increase in number of patients affected by 2030.

A pharmacological treatment option for dry eye disease is cyclosporine. Cyclosporine is available, at least in the US as an approved medicine in the form of an ophthalmic (o/w) emulsion (Restasis®). This product is indicated to increase tear production in patients whose tear production is presumed to be suppressed due to ocular inflammation associated with keratoconjunctivitis sicca.

WO2011/073134 A1 discloses pharmaceutical compositions in the form of solutions comprising cyclosporine and a semifluorinated alkane as a liquid vehicle which may be administered to the eye of a patient, such as for the treatment of keratoconjunctivitis sicca, for instance compositions comprising cyclosporine in semifluorinated alkane 1-(perfluorobutyl)pentane (F4H5) in the presence of ethanol as a co-solvent.

Gehlsen et al. (Investigative Ophthalmology & Visual Science June 2015, Vol. 56, 319) describes a study to test the use of CsA in (F4H5) for topical therapy in a mouse model of experimental dry eye disease. Gehlsen et al describes that in the study, topical therapy was performed on mice with induced experimental dry eye disease 3×/day (5 µL/eye). Gehlsen et al. however does not disclose a treatment or dosing regimen for the treatment of dry eye disease in human subjects.

WO2018/115097 describes a dosing regimen for the treatment of patients with dry eye disease, based on ophthalmic compositions comprising about 0.05 to 0.1% (w/v) cyclosporine dissolved in 1-(perfluorobutyl)pentane. This document however does not disclose a targeted treatment in respect of specific symptoms associated with dry eye disease and the frequency of their occurrence. The method of treatment also does not disclose a composition for use in a treatment of patients meeting a specific set of dry eye disease signs and symptoms.

Accordingly there is still a need for means and method for treating patients meeting certain criteria for dry eye disease, as well as for treating patients for which certain symptoms of dry eye disease is particularly prevalent. It is thus an object of the present invention to provide composition for use which is effective in addressing these specific aspects. Further objects of the invention will be clear on the basis of the following description of the invention, examples and claims.

SUMMARY OF THE INVENTION

In a first aspect, the invention relates to an ophthalmic composition comprising 0.1% (w/v) cyclosporine dissolved in 1-(perfluorobutyl)pentane for use in a method of treating keratoconjunctivitis sicca (dry eye disease), wherein the method comprises a step of topically administering the composition to an eye of a patient, and wherein the patient has a total ocular surface disease index (OSDI) score of equal or greater than 45. In other embodiments, the patient has a total ocular surface disease index (OSDI) score of equal or greater than 55.

In a second aspect, the invention relates to an ophthalmic composition comprising 0.1% (w/v) cyclosporine dissolved in 1-(perfluorobutyl)pentane for use in: a) a method of treating and/or ameliorating the symptoms associated with keratoconjunctivitis sicca (dry eyes), wherein the symptoms are dryness and blurred vision; and/or b) for use in a method of treating and/or ameliorating the awareness of symptoms of dry eyes and the frequency of dryness.

DETAILED DESCRIPTION OF THE INVENTION

Figure 1:
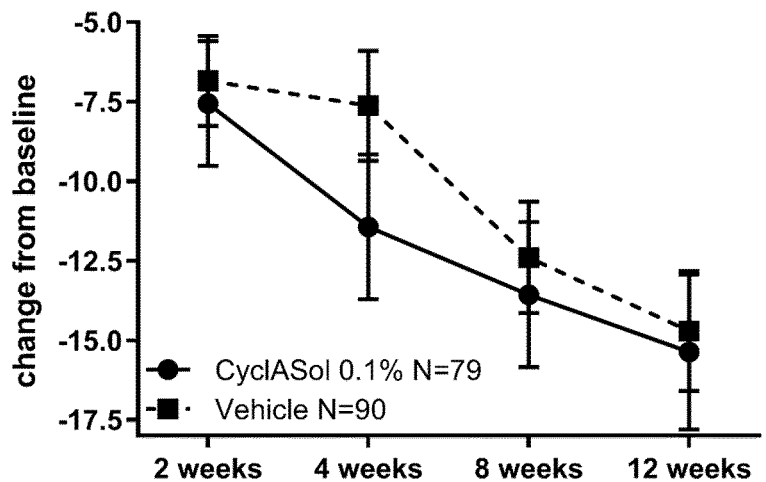
FIG. 1. Total ocular surface disease index (OSDI)—depicted is the change from baseline of the total OSDI score (mean) at 2 weeks, 4 weeks, 8 weeks and 12 weeks of treatment (2 times per day) with vehicle (F4H5; N=90) and CyclASol 0.1% Ophthalmic Solution (clear ophthalmic solution of Cyclosporine A dissolved in 1-(perfluorobutyl)pentane, with 1.0% w/w ethanol; N=79), in subjects with a baseline total OSDI of 45 or greater.

The present invention relates to, in a first aspect, an ophthalmic composition comprising 0.1% (w/v) cyclosporine dissolved in 1-(perfluorobutyl)pentane for use in a method of treating of keratoconjunctivitis sicca (dry eye disease), wherein the method comprises a step of topically administering the composition to an eye of a patient, and wherein the patient has a total ocular surface disease index (OSDI) score of equal or greater than 45.

Dry eye disease (also abbreviated as DED, and which also may be known as keratoconjunctivitis sicca, dysfunctional tear syndrome or dry eye syndrome) is a complex disease that results in symptoms of discomfort, visual disturbance, and tear film instability, and which creates potential for damage of the ocular surface. It may be accompanied by increased osmolarity of the tear film and inflammation of the ocular surface. A patient having keratoconjunctivitis sicca may experience any one of, or a combination of tear hyperosmolarity, tear film instability or abnormalities in the lipid layer composition of the tear film.

Two major categories of keratoconjunctivitis sicca or dry eye disease (DED) are distinguished today, which are aqueous-deficient DED and evaporative DED. Within the class of aqueous-deficient forms of DED, two major subtypes may be differentiated, Sjögren and non-Sjögren.

Sjögren syndrome patients suffer from autoimmune disorders in which the lacrimal glands are invaded by activated T-cells, which leads not only to dry eye disease but also to a dry mouth condition. The Sjögren syndrome can be a primary disease or can result from other autoimmune diseases, such as systemic lupus erythrematosus or rheumatoid arthritis. Non-Sjögren patients suffering from an aqueous-deficient DED usually have a lacrimal gland insufficiency, lacrimal duct obstruction or reflex hyposecretion.

The second major class, evaporative dry eye disease, is also somewhat heterogeneous and can develop as a result of diverse root causes. One of the major causes is meibomian gland disease or dysfunction, eyelid aperture disorders, blink disorders (as in Parkinson's disease) or ocular surface disorders (as in allergic conjunctivitis).

Symptoms of dry eye disease may include, but are not limited to, any one, or combination of, the following: a dry, scratchy, gritty, or sandy feeling in the eye; foreign body sensation; pain or soreness; stinging or burning; itching; increased blinking; eye fatigue; photophobia; blurry vision; redness; mucus discharge; contact lens intolerance; and excessive reflex tearing. It is understood that not all patients suffering from dry eye disease may exhibit all of these symptoms simultaneously.

Subjects suffering from dry eye disease may experience symptoms which individually, or collectively, such as blurring, pain, irritation which may contribute to visual impairment or difficulties which can be reflected by a negative effect on the subject's performance in functional tasks where visual performance and acuity may be essential. Dry eye disease may also lead, or contribute to corneal surface damage for example to the central cornea.

As understood herein, the term "dry eye disease" individually may refer to any one or combination of the subtypes or categories, or root causes as described herein and that any symptom or aspect or pathophysiological consequences of dry eye disease may be addressed.

The severity of dry eye disease in subjects or patients can be classified and scored using one or more, or a combination of standard tests based on assessment of dry eye disease symptoms. For example, the severity of dry eye disease may be determined using tests based on the assessment of patient perception of ocular symptoms and their effect on vision, based on questionnaires such as the Ocular Surface Disease Index (OSDI) questionnaire, which is a 12-item questionnaire focussed on symptoms of ocular irritation associated with dry eye disease and their impact on daily activities and lifestyle of the patient during the week preceding their assessment.

The OSDI test is scored using a scale of 0 to 4 for each question. For example, as part of the test patients may be asked questions regarding problems with blurred vision during the last week, and are asked to indicate, if applicable, either 0 for none of the time, 1 for some of the time, 2 for half of the time, 3 for most of the time or 4 for all of the time. The scores from the questionnaire are totalled and assessed on a scale of 0 to 100, with higher scores representing greater degree/severity and impact of dry eye disease. In the context of the present invention, it has been found that the compositions as defined are particularly effective especially in the treatment of dry eye disease in patients having at baseline, prior to commencement of treatment with the composition, a total OSDI score of equal, or greater than 45; or patients with a total OSDI score of equal, or greater than 55.

The dry eye symptom visual analogue scale (VAS) is a test in the form of a questionnaire, where subjects are asked to rate their ocular symptoms (both eyes simultaneously) by placing a vertical mark on the horizontal line to indicate the level of discomfort from a scale of 0 to 100% with regards to dryness, sticky feeling, burning/stinging, foreign body sensation, itching, blurred vision, sensitivity to light, and pain, wherein 0 corresponds to "no discomfort" while 100% corresponds to "maximal discomfort". The VAS test also assesses the frequency in occurrence of dryness experienced by the subject, as well as the percentage of time the subject is aware of experiencing the symptoms of dry eye, (with 0 corresponding to 'never' and 100% corresponding to 'all of the time'). The VAS test may be conducted at various time points to assess the effectiveness and patient response in respect to impact of therapy on these symptoms of dry eye disease.

Signs of dry eye disease in a patient's eye may also be evaluated and determined using any combination of objective clinical measures such as the Schirmer test type 1, fluorescein staining and/or lissamine green staining of the cornea and conjunctiva, and tear-film break up time (TFBUT, or TBUT) as a measurement of tear quality. Therapeutic efficacy may also be assessed by comparison of measurements for each or combination of these clinical measures, obtained at various time points during a given treatment period, also in combination or conjunction with any of the symptom assessments described above.

In one embodiment of the invention described herein, the subject or patient has, prior to treatment with the compositions defined herein, a total OSDI scoring of equal or greater than 45, or preferably equal or greater than 55, as well as, in at least one eye, or alternatively both eyes, any one or combination of the following:

i. a total corneal fluorescein staining score of ≥10 according to NEI grading (i.e. sum of scoring for the inferior, superior, central, nasal, and temporal cornea regions equal to or greater than 10);
ii. a total lissamine green conjunctival score (sum of temporal and nasal regions) of ≥2 according to the Oxford scale;
iii. a Schirmer's Test I score of between 1 mm and 10 mm or any combination thereof.

Cyclosporine is a pharmacological treatment option for dry eye disease, which is available as a prescription medication, for example, in the US in the form of an 0.05% ophthalmic (o/w) emulsion (Restasis®). This product is indicated to increase tear production in patients whose tear production is presumed to be suppressed due to ocular inflammation associated with keratoconjunctivitis sicca. Restasis® is administered twice a day in each eye approximately 12 hours apart. It is packaged in single-vials. (Prescribing Information, Restasis®).

Cyclosporine (synonyms include cyclosporin A, CsA, or ciclosporin) is a cyclic nonribosomal peptide comprising 11 amino acids with the empirical formula $C_{62}H_{111}N_{11}O_{12}$ and molecular weight of 1202.61. It is an immunosuppressant drug that is widely used in post-allergenic organ transplant, to reduce the activity of the patient's immune system and thereby, the risk of organ rejection. Cyclosporine is typically provided as a colourless or white powder. Cyclosporine is thought to bind to the cytosolic protein cyclophilin (immunophilin) of immunocompetent lymphocytes, especially T-lymphocytes. This complex of cyclosporin and cyclophilin inhibits calcineurin, which, under normal circumstances, is responsible for activating the transcription of interleukin 2. It also inhibits lymphokine production and interleukin release and, therefore, leads to a reduced function of effector T-cells.

The ophthalmic composition according to the present invention employs, as a liquid vehicle for the cyclosporine, the compound 1-(perfluorobutyl)pentane. 1-(perfluorobutyl)pentane is a semifluorinated alkane with the chemical formula $F(CF_2)_4(CH_2)_5H$. It is an inert, water-insoluble liquid, with a density of 1.284 g/cm$^3$ at 25° C. and refractive index of 1.3204 at 20° C. Alternative nomenclature for this compound includes F4H5, wherein F denotes a linear perfluorinated alkane segment comprising 4 carbon atoms and wherein H denotes a linear and non-fluorinated alkane hydrocarbon segment of 5 carbon atoms. Preferably, the 1-(perfluorobutyl)pentane is substantially free of water.

In one embodiment, the ophthalmic composition for any one of the uses according to the present invention may comprise or consist, further to the cyclosporine featured in any one the preferred concentrations of the invention, of at least about 97% (w/w) or more preferably, of at least about 98% (w/w), or of at least about 99% (w/w) of 1-(perfluorobutyl)pentane, based on the total weight of the ophthalmic composition (final dosage form). In another embodiment, the pharmaceutical composition for any one of the uses according to the present invention may consist of, in addition to the cyclosporine in an amount or concentration as defined herein, from about 95.0 to about 99.99% (w/w), or about 96.0 to about 99.99% (w/w), or from about 98.0 to 99.99% (w/w), or from about 99.999 to about 99.9999% (w/w) of 1-(perfluorobutyl)pentane, based on the total weight of the final composition.

In another embodiment, the ophthalmic composition for any one of the uses described herein for the present invention may optionally further comprise 2-(perfluorobutyl)pentane. The composition, in addition to 1-(perfluorobutyl) pentane, may optionally comprise minor amounts of 2-(perfluorobutyl)pentane, of up to 2% (w/w), or up to 1% (w/w), or up to 0.5% (w/w).

The concentration of cyclosporine in the ophthalmic compositions for any one of the uses according to the invention is 0.1% (w/v) of the composition.

Unless otherwise indicated, the term "% (w/v)" denotes the amount of a component of a composition as a weight percentage in relation to the total volume of the composition (with 'w' denoting the weight and 'v' denoting volume). For example 0.1% (w/v) would correspond to 1.0 mg of a component in 1 mL of the composition. Unless otherwise indicated, the term "% (w/w)" or wt % refers to the amount of a component of a composition as a weight percentage in relation to the total weight of the composition (with 'w' denoting weight).

The term 'about' as used herein and in reference or connection to a parameter, for example such as the concentration of cyclosporine dissolved in the composition or the volume featured in a single dose or applied liquid drop of the composition includes the precise value as defined, as well as any value falling within the degree of variability usually observed in measuring or determining these parameters using the standard techniques and equipment known in the art and field.

The ophthalmic composition as defined herein may be used for the treatment of human subjects with dry eye disease, as well as for any related conditions, or signs and symptoms associated therewith.

In a first aspect, the present invention provides for the following items:

1.1 An ophthalmic composition comprising 0.1% (w/v) cyclosporine dissolved in 1-(perfluorobutyl)pentane for use in a method of treating keratoconjunctivitis sicca (dry eye disease), wherein the method comprises a step of topically administering the composition to an eye of a patient, wherein the patient has a total ocular surface disease index (OSDI) score of equal or greater than 45.

1.2 Composition for use of 1.1, wherein the patient has a total ocular surface disease index (OSDI) score of equal or greater than 55.

1.3 The ophthalmic composition for use of any one of the preceding items, wherein the composition comprises up to about 1.0% (w/w) ethanol.

1.4 The ophthalmic composition for use of any one of the preceding items, wherein the composition consists of 0.1% (w/v) cyclosporine, 1-(perfluorobutyl)pentane (F4H5) and up to 1.0% (w/w) ethanol.

1.5 The composition for use of any of the preceding items, wherein the ophthalmic composition is administered to the surface of the cornea and/or conjunctiva in the form of a liquid drop.

1.6 The composition for use in any of the preceding items, wherein the composition is administered as a single drop having a volume of about 8 to 11 μL, preferably of about 8 to 10 μL.

1.7 The composition for use of any of the preceding items, wherein the composition is administered in a dose of a single drop per eye one time per day in volume of about 8-10 μL.

1.8 The ophthalmic composition for use according to any one of the preceding items, wherein the composition is administered as a single drop having a volume of about 10 μl.

1.9 The ophthalmic composition for use of any one of the preceding items, wherein the composition is administered twice a day per eye.

1.10 The composition for use in any of the preceding items, wherein the composition is administered in a dose of a single drop per eye twice per day in net volume of about 16-20 μL.

1.11 The composition for use according to any one of the preceding items, wherein the dry eye disease is aqueous-deficient dry eye disease.

1.12 The composition for use according to any of the preceding items, wherein the dry eye disease is evaporative dry eye disease.

1.13 The composition for use according to any of the preceding items, wherein the patient is non-responsive, or insufficiently responsive, to treatment with aqueous ophthalmic eye drop compositions (e.g. aqueous cyclosporin emulsion eye drops).

1.14 The composition for use of any of the preceding items, wherein the time interval between topical administration of the composition to the eye or eye surface of a first dose and a second dose is at least 4 hours, or at least 6 hours, or at least 12 hours.

1.15 The composition for use of any of the preceding items, wherein the duration of the treatment is for at least 2 weeks, or at least 4 weeks, or at least 6 weeks, or at least 8 weeks, or at least 12 weeks.

1.16 The composition for use of any of the preceding items wherein the patient is a human patient.

1.17 The composition for use of any of the preceding items, wherein the patient is a female patient.

1.18 The composition for use of any of the preceding items, wherein the patient is a male patient.

1.19 The composition for use of any of the preceding items, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

1.20 The composition for use of any of the preceding items, wherein the patient suffers from a co-morbidity, for example, conjunctivitis, stye, chalazion, blepharitis, ectropion, eyelid laxity, eyelid edema, eyelid dermatitis, punctate keratopathy, or ocular allergies, or any combination thereof.

1.21 The composition for use of any of the preceding items, wherein the patient suffers from keratoconjunctivitis sicca which is caused by treatment of a co-morbidity, for example, treatment with any one or more of: isotretinoin, sedatives, diuretics, tricyclic antidepressants, antihypertensives, anticholinergics, oral contraceptives, antihistamine, nasal decongestants, beta-adrenergic antagonists, phenothiazines, atropine opiates (e.g., morphine), optionally wherein any such treatment is concurrent or previous, and further optionally, wherein any such treatment is systemic (e.g., oral or parenteral).

1.22 The composition for use of any of the preceding items, wherein the patient suffers from keratoconjunctivitis sicca which is caused by ocular surgical intervention, for example, corneal surgery, refractive surgery, LASIK surgery, cataract surgery, optionally wherein any such ocular surgery is concurrent or previous.

1.23 The composition for use of any of the preceding items, wherein the patient is concomitantly under treatment with another topical ophthalmic medication, for example, an antibiotic, antifungal, corticosteroid, another immunosuppressant, sympathomimetic, anesthetic, antihistamine, or any combination thereof.

1.24 The composition for use of any of the preceding items, wherein the patient is a contact lens wearer.

1.25 The composition for use of any of the preceding items, wherein the patient was unresponsive or insufficiently response to previous treatment for keratoconjunctivitis sicca (dry eye disease).

1.26 The composition for use of 1.25, wherein said previous treatment comprises one or more of the following treatment methods: topical aqueous immunosuppressant administration, (e.g., topical aqueous ciclosporin), topical corticosteroid administration, or topical aqueous artificial tears administration.

1.27 The composition for use of any of the preceding items, wherein the patient has at least one eye with a total corneal fluorescein staining score at least equal or higher than 10.

1.28 The composition for use of any of the preceding items, wherein the patient has at least one eye with any one or combination of criteria (e.g. signs of dry eye disease) selected from the group consisting of:
  i. A total lissamine green conjunctival score (sum of temporal and nasal regions) of ≥2 according to the Oxford scale;
  ii. a total corneal fluorescein staining (NEI scale) of ≥10 (i.e. sum of inferior, superior, central, nasal and temporal regions);
  iii. an unanesthetized Schirmer's Test score between 1 mm and 10 mm.

1.29 The composition for use according to item 1.28, wherein the patient has at least one eye (i.e. the same eye) which meets criteria (i), (ii) and (iii).

1.30 The composition for use according to any one of the preceding items, wherein the patient has at least one eye, or both eyes with any one or combination of:
  i. a central corneal fluorescein staining (NEI scale) score of 2 or higher,
  ii. an inferior corneal fluorescein staining (NEI scale) score of 2 or higher,
  iii. a total corneal fluorescein staining (NEI scale) score of 11 or higher.
1.31 The composition for use of any of the preceding items, wherein the patient has a history of keratoconjunctivitis sicca (dry eye disease) in one or both eyes for at least six months.
1.32 The composition for use of any of the preceding items, wherein the composition is effective in reducing one or more signs and/or symptoms of keratoconjunctivitis sicca (dry eye disease), preferably wherein the one or more signs and/or symptoms is selected from ocular surface damage.
1.33 The composition for use of any of the preceding items, wherein the composition is effective in reducing the one or more signs and/or symptoms of keratoconjunctivitis sicca (dry eye disease) within 2 weeks, within 4 weeks, or within 8 weeks after first administration of the composition/commencement of treatment.
1.34 The composition for use in in any of the preceding items, wherein the composition is effective in reducing ocular surface damage.
1.35 The composition for use according to 1.32 to 1.34, wherein the ocular surface damage is selected from the group consisting of:
  i. surface damage of the total corneal region;
  ii. surface damage of the central corneal region;
  iii. surface damage of the nasal corneal region;
  iv. surface damage of the temporal corneal region;
  v. surface damage of the inferior corneal region; and
  vi. combinations thereof.
1.36 The composition for use of 1.35, wherein the ocular surface damage is selected from ocular surface damage in the central corneal region and ocular surface damage of the inferior corneal region.
1.37 The composition for use of 1.32 to 1.36 wherein the reduction of ocular surface damage is determined by corneal fluorescein staining (NEI scale).
1.38 The composition for use of 1.37, wherein the corneal fluorescein staining method is selected from the group consisting of:
  iv. total corneal fluorescein staining;
  v. central corneal fluorescein staining;
  vi. nasal corneal fluorescein staining;
  vii. temporal fluorescein staining;
  viii. inferior corneal fluorescein staining; and
  ix. any combination thereof.
1.39 The composition for use of 1.32 to 1.38, wherein the treatment is effective in reducing the total corneal fluorescein staining score (sum of inferior, superior, central, nasal, and temporal staining scores; NEI scale) by an integer of at least 2, or by at least 3 points, optionally within a treatment period of at least 8 weeks, or at least 12 weeks.
1.40 The composition for use of any of the preceding items, wherein the composition is effective in treating one or more ocular symptoms of keratoconjunctivitis sicca (dry eye disease) selected from (x) dryness, (xi) sticky feeling, (xii) burning/stinging, (xiii) foreign body sensation, (xiv) itching, (xv) blurred vision, (xvi) sensitivity to light, (xvii) pain, and (xviii) any combination thereof.

1.41 The composition for use of any of the preceding items, wherein the composition is effective in reducing the (xix) frequency of dryness, (xx) awareness of symptoms of dry eye and (xxi) the severity of dryness and (xxi) any combination thereof.
1.42 The composition for use of item 1.41, wherein the composition is effective in reducing the severity of dryness or the frequency of dryness or the combination thereof.
1.43 The composition for use of any preceding items, wherein the method of treatment comprises the reduction of ocular surface damage, e.g. ocular surface damage of the cornea, or ocular surface damage selected from: i. surface damage of the total corneal region; ii. surface damage of the central corneal region; iii. surface damage of the nasal corneal region; iv. surface damage of the temporal corneal region; v. surface damage of the inferior corneal region; and vi. combinations thereof
1.44 The composition for use of item 1.43, wherein the ocular surface damage is selected from ocular surface damage in the central corneal region and ocular surface damage of the inferior corneal region.
1.45 The composition for use of item 1.43-1.44 wherein the ocular surface damage is determined by corneal fluorescein staining (NEI scale).
1.46 The composition for use of any of the preceding items, wherein the patient has at least one eye with any one or combination of criteria selected from the group consisting of:
  a total corneal fluorescein staining value in the range of 10 to 15, preferably 10 to 13 (NEI scale);
  a central corneal fluorescein staining value in the range of 1 to 3 (NEI scale); preferably 2 to 3 (NEI scale);
  a total lissamine green conjunctival staining score in the range of 2 to 6, preferably 3 to 5;
  an unanesthetized Schirmer's test score in the range of 2 to 8 mm.
1.47 The composition for use of any of the preceding items, wherein the patient does not suffer from meibomian gland dysfunction and/or blepharitis.
1.48 The composition for use of any of the preceding items, wherein the patient has an unanesthetized Schirmer's Test score in the range of 3 to 7 mm, preferably in the range of 4 to 6 mm, more preferably of about 5 mm.
1.49 The composition for use of any of the preceding items, wherein the patient has at least one eye with a total corneal fluorescein staining score at least equal or higher than 11 (NEI scale).
1.50 The composition for use of any of the preceding items, wherein the patient has at least one eye with a central corneal fluorescein staining value in the range of 1 to 3 (NEI scale).
1.51 The composition for use of any of the preceding items, wherein the patient has at least one eye with a total lissamine green conjunctival staining score in the range of 2 to 6.
1.52 The composition for use of any of the preceding items, wherein the patient has at least one eye with an unanesthetized Schirmer's test score in the range of 4 to 6 mm.
1.53 The composition for use of any of the preceding items, wherein the central corneal fluorescein staining value is about 3 (NEI scale).
1.54 The composition for use of any of the preceding items, wherein the lissamine green conjunctival staining score is in the range of 3 to 5.

1.55 The composition for use of any of the preceding items, wherein the unanesthetized Schirmer's test score is about 5 mm.

1.56 An ophthalmic composition comprising 0.1% (w/v) cyclosporine dissolved in 1-(perfluorobutyl)pentane for use in a method of treating keratoconjunctivitis sicca (dry eye disease), wherein the method comprises a step of topically administering the composition to an eye of a patient, wherein the patient has at least one eye with a total corneal fluorescein staining score at least equal or higher than 11 (NEI scale).

1.57 An ophthalmic composition comprising 0.1% (w/v) cyclosporine dissolved in 1-(perfluorobutyl)pentane for use in a method of treating keratoconjunctivitis sicca (dry eye disease), wherein the method comprises a step of topically administering the composition to an eye of a patient, wherein the patient has a total ocular surface disease index (OSDI) score of equal or greater than 45, and wherein the patient has at least one eye with a total corneal fluorescein staining score at least equal or higher than 11 (NEI scale).

1.58 An ophthalmic composition comprising 0.1% (w/v) cyclosporine dissolved in 1-(perfluorobutyl)pentane for use in a method of treating keratoconjunctivitis sicca (dry eye disease), wherein the method comprises a step of topically administering the composition to an eye of a patient, wherein the patient has a total ocular surface disease index (OSDI) score of equal or greater than 45, and wherein the patient has at least one eye with:
a total corneal fluorescein staining score at least equal or higher than 11 (NEI scale); and
a central corneal fluorescein staining value in the range of 1 to 3 (NEI scale).

1.59 An ophthalmic composition comprising 0.1% (w/v) cyclosporine dissolved in 1-(perfluorobutyl)pentane for use in a method of treating keratoconjunctivitis sicca (dry eye disease), wherein the method comprises a step of topically administering the composition to an eye of a patient, wherein the patient has a total ocular surface disease index (OSDI) score of equal or greater than 45, and wherein the patient has at least one eye with:
a total corneal fluorescein staining score at least equal or higher than 11 (NEI scale);
a central corneal fluorescein staining value in the range of 1 to 3 (NEI scale); and
a total lissamine green conjunctival staining score in the range of 2 to 6.

1.60 An ophthalmic composition comprising 0.1% (w/v) cyclosporine dissolved in 1-(perfluorobutyl)pentane for use in a method of treating keratoconjunctivitis sicca (dry eye disease), wherein the method comprises a step of topically administering the composition to an eye of a patient, wherein the patient has a total ocular surface disease index (OSDI) score of equal or greater than 45, and wherein the patient has at least one eye with:
a total corneal fluorescein staining score at least equal or higher than 11 (NEI scale);
a central corneal fluorescein staining value in the range of 1 to 3 (NEI scale);
a total lissamine green conjunctival staining score in the range of 2 to 6; and
an unanesthetized Schirmer's test score in the range of 4 to 6 mm.

1.61 The composition for use in any one of items 1.58 to 1.60, wherein the central corneal fluorescein staining value is about 3 (NEI scale).

1.62 The composition for use in any one of items 1.59 to 1.61, wherein the lissamine green conjunctival staining score is in the range of 3 to 5.

1.63 The composition for use in any one of items 1.60 to 1.62, wherein the unanesthetized Schirmer's test score is about 5 mm.

1.64 The composition for use in any one of items 1.57 to 1.63, wherein the patient has a total ocular surface disease index (OSDI) score of equal or greater than 55.

1.65 The composition for use in any one of items 1.49 to 1.64, wherein the patient has the total corneal fluorescein staining score, the central corneal fluorescein staining value, the lissamine green conjunctival staining score, and/or the unanesthetized Schirmer's test score with the specified values in both eyes.

In a second aspect the present disclosure may relate to a method of treatment according to the following:

2.1 A method of treating keratoconjunctivitis sicca (dry eye disease) comprising a step of topically administering an ophthalmic composition comprising 0.1% (w/v) cyclosporine dissolved in 1-(perfluorobutyl)pentane to an eye of a patient, wherein the patient has a total ocular surface disease index (OSDI) score of equal or greater than 45.

2.2 Method 2.1, wherein the patient has a total ocular surface disease index (OSDI) score of equal or greater than 55.

2.3 Any preceding method, wherein the composition comprises up to about 1.0% (w/w) ethanol.

2.4 Any preceding method, wherein the composition consists of about 0.1% (w/v) cyclosporine, F4H5 and up to about 1.0% (w/w) ethanol.

2.5 Any preceding method, wherein the ophthalmic composition is administered to the surface of the cornea and/or conjunctiva in the form of a liquid drop.

2.6 Any preceding method, wherein the composition is administered as a single drop having a volume of about 8 to 11 µL, preferably of about 8 to 10 µL.

2.7 Any preceding method, wherein the composition is administered in a dose of a single drop per eye one time per day in volume of 8-10 µL.

2.8 Any preceding method, wherein the composition is administered as a single drop having a volume of about 10 µl.

2.9 Any preceding method, wherein the composition is administered twice per day per eye.

2.10 Any preceding method, wherein the composition is administered in a dose of a single drop per eye twice per day in net volume of about 16-20 µL.

2.11 Any preceding method, wherein the dry eye disease is aqueous-deficient dry eye disease.

2.12 Any preceding method, wherein the dry eye disease is evaporative dry eye disease.

2.13 Any preceding method, wherein the patient is non-responsive, or insufficiently responsive to treatment with aqueous ophthalmic eye drop compositions (e.g. aqueous cyclosporin emulsion eye drops).

2.14 Any preceding method, wherein the time interval between topical administration of the composition to the eye or eye surface of a first dose and a second dose is at least 4 hours, or at least 6 hours, or at least 12 hours.

2.15 Any preceding method, wherein the duration of the treatment is for at least 2 weeks, or at least 4 weeks, or at least 6 weeks, or at least 8 weeks, or at least 12 weeks.

2.16 Any preceding method, wherein the patient is a human patient.

2.17 Any preceding method, wherein the patient is a female patient.

2.18 Any preceding method, wherein the patient is a male patient.

2.19 Any preceding method, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

2.20 Any preceding method, wherein the patient suffers from a co-morbidity, for example, conjunctivitis, stye, chalazion, blepharitis, ectropion, eyelid laxity, eyelid edema, eyelid dermatitis, punctate keratopathy, or ocular allergies, or any combination thereof.

2.21 Any preceding method, wherein the patient suffers from keratoconjunctivitis sicca which is caused by treatment of a co-morbidity, for example, treatment with any one or more of: isotretinoin, sedatives, diuretics, tricyclic antidepressants, antihypertensives, anticholinergics, oral contraceptives, antihistamine, nasal decongestants, beta-adrenergic antagonists, phenothiazines, atropine opiates (e.g., morphine), optionally wherein any such treatment is concurrent or previous, and further optionally, wherein any such treatment is systemic (e.g., oral or parenteral).

2.22 Any preceding method, wherein the patient suffers from keratoconjunctivitis sicca which is caused by ocular surgical intervention, for example, corneal surgery, refractive surgery, LASIK surgery, cataract surgery, optionally wherein any such ocular surgery is concurrent or previous.

2.23 Any preceding method, wherein the patient is concomitantly under treatment with another topical ophthalmic medication, for example, an antibiotic, antifungal, corticosteroid, another immunosuppressant, sympathomimetic, anesthetic, antihistamine, or any combination thereof.

2.24 Any preceding method, wherein the patient is a contact lens wearer.

2.25 Any preceding method, wherein the patient was unresponsive or insufficiently response to previous treatment for keratoconjunctivitis sicca (dry eye disease).

2.26 Method 2.25, wherein said previous treatment comprise one or more of the following treatment methods: topical aqueous immunosuppressant administration, (e.g., topical aqueous ciclosporin), topical corticosteroid administration, or topical aqueous artificial tears administration.

2.27 Any preceding method, wherein the patient has at least one eye with a total corneal fluorescein staining score of at least equal or higher than 10.

2.28 Any preceding method, wherein the patient has at least one eye with any one or combination of criteria (e.g. signs of dry eye disease) selected from the group consisting of:
  i. A total lissamine green conjunctival score (sum of temporal and nasal regions) of 2 according to the Oxford scale;
  ii. a total corneal fluorescein staining (NEI scale) of 10 (i.e. sum of inferior, superior, central, nasal and temporal regions);
  iii. an unanesthetized Schirmer's Test score between 1 mm and 10 mm.

2.29 Method 2.28, wherein the patient has at least one eye (i.e. the same eye) which meets criteria (i), (ii) and (iii).

2.30 Any preceding method, wherein the patient has at least one eye, or both eyes with any one or combination of:
  i. a central corneal fluorescein staining (NEI scale) score of 2 or higher,
  ii. an inferior corneal fluorescein staining (NEI scale) score of 2 or higher,
  iii. a total corneal fluorescein staining (NEI scale) score of 11 or higher.

2.31 Any preceding method, wherein the patient has a history of keratoconjunctivitis sicca (dry eye disease) in one or both eyes for at least six months.

2.32 Any preceding method, wherein the composition is effective in reducing one or more signs and/or symptoms of keratoconjunctivitis sicca (dry eye disease), preferably wherein the one or more signs and/or symptoms is selected from ocular surface damage.

2.33 Any preceding method, wherein the composition is effective in reducing the one or more signs and/or symptoms of keratoconjunctivitis sicca (dry eye disease) within 2 weeks, within 4 weeks, or within 8 weeks after first administration of the composition/commencement of treatment.

2.34 Any preceding method, wherein the composition is effective in reducing ocular surface damage.

2.35 Method 2.32 to 2.34, wherein the ocular surface damage is selected from the group consisting of:
  i. surface damage of the total corneal region;
  ii. surface damage of the central corneal region;
  iii. surface damage of the nasal corneal region;
  iv. surface damage of the temporal corneal region;
  v. surface damage of the inferior corneal region; and
  vi. combinations thereof.

2.36 Method 2.35, wherein the ocular surface damage is selected from ocular surface damage in the central corneal region and ocular surface damage of the inferior corneal region.

2.37 Method 2.32 to 2.36 wherein the reduction of ocular surface damage is determined by corneal fluorescein staining (NEI scale).

2.38 Method 2.37, wherein the corneal fluorescein staining method is selected from the group consisting of:
  iv. total corneal fluorescein staining;
  v. central corneal fluorescein staining;
  vi. nasal corneal fluorescein staining;
  vii. temporal fluorescein staining;
  viii. inferior corneal fluorescein staining; and
  ix. any combination thereof.

2.39 Method 2.32 to 2.38, wherein the treatment is effective in reducing the total corneal fluorescein staining score (sum of inferior, superior, central, nasal, and temporal staining scores; NEI scale) by an integer of at least 2, or by at least 3 points, optionally within a treatment period of at least 8 weeks, or at least 12 weeks.

2.40 Any preceding method, wherein the composition is effective in treating one or more ocular symptoms of keratoconjunctivitis sicca (dry eye disease) selected from (x) dryness, (xi) sticky feeling, (xii) burning/stinging, (xiii) foreign body sensation, (xiv) itching, (xv) blurred vision, (xvi) sensitivity to light, (xvii) pain, (xviii) and any combination thereof.

2.41 Any preceding method, wherein the composition is effective in reducing the (xix) frequency of dryness, (xx) awareness of symptoms and (xxi) the severity of dryness and (xxi) any combination thereof.

2.42 Method 2.40 to 2.41, wherein the composition is effective in reducing the severity of dryness or the frequency of dryness or the combination thereof.

2.43 Any preceding method, wherein the method of treatment comprises the reduction of ocular surface damage, e.g. ocular surface damage of the cornea, or ocular surface damage selected from: i. surface damage of the total corneal region; ii. surface damage of the central corneal region; iii. surface damage of the nasal corneal region; iv.

surface damage of the temporal corneal region; v. surface damage of the inferior corneal region; and vi. combinations thereof.

2.44 Method 2.43, wherein the ocular surface damage is selected from ocular surface damage in the central corneal region and ocular surface damage of the inferior corneal region.

2.45 Method 2.43 to 2.44 wherein the ocular surface damage is determined by corneal fluorescein staining (NEI scale).

2.46 Any preceding method, wherein the patient has at least one eye with any one or combination of criteria selected from the group consisting of:
a total corneal fluorescein staining value in the range of 10 to 15, preferably 10 to 13 (NEI scale);
a central corneal fluorescein staining value in the range of 1 to 3 (NEI scale);
preferably 2 to 3 (NEI scale);
a total lissamine green conjunctival staining score in the range of 2 to 6, preferably 3 to 5;
an unanesthetized Schirmer's test score in the range of 2 to 8 mm.

2.47 Any preceding method, in which the patient does not suffer from blepharitis and/or meibomian gland dysfunction.

2.48 Any preceding method, wherein the patient has an unanesthetized Schirmer's Test score in the range of 3 to 7 mm, preferably in the range of 4 to 6 mm, more preferably of about 5 mm.

2.49 Any preceding method, wherein the patient has at least one eye with a total corneal fluorescein staining score at least equal or higher than 11 (NEI scale).

2.50 Any preceding method, wherein the patient has at least one eye with a central corneal fluorescein staining value in the range of 1 to 3 (NEI scale).

2.51 Any preceding method, wherein the patient has at least one eye with a total lissamine green conjunctival staining score in the range of 2 to 6.

2.52 Any preceding method, wherein the patient has at least one eye with an unanesthetized Schirmer's test score in the range of 4 to 6 mm.

2.53 Any preceding method, wherein the central corneal fluorescein staining value is about 3 (NEI scale).

2.54 Any preceding method, wherein the lissamine green conjunctival staining score is in the range of 3 to 5.

2.55 Any preceding method, wherein the unanesthetized Schirmer's test score is about 5 mm.

2.56 A method of treating keratoconjunctivitis sicca (dry eye disease) comprising a step of topically administering an ophthalmic composition comprising 0.1% (w/v) cyclosporine dissolved in 1-(perfluorobutyl)pentane to an eye of a patient, wherein the patient has at least one eye with a total corneal fluorescein staining score at least equal or higher than 11 (NEI scale).

2.57 A method of treating keratoconjunctivitis sicca (dry eye disease) comprising a step of topically administering an ophthalmic composition comprising 0.1% (w/v) cyclosporine dissolved in 1-(perfluorobutyl)pentane to an eye of a patient, wherein the patient has a total ocular surface disease index (OSDI) score of equal or greater than 45, and wherein the patient has at least one eye with a total corneal fluorescein staining score at least equal or higher than 11 (NEI scale).

2.58 A method of treating keratoconjunctivitis sicca (dry eye disease) comprising a step of topically administering an ophthalmic composition comprising 0.1% (w/v) cyclosporine dissolved in 1-(perfluorobutyl)pentane to an eye of a patient, wherein the patient has a total ocular surface disease index (OSDI) score of equal or greater than 45, and wherein the patient has at least one eye with:
a total corneal fluorescein staining score at least equal or higher than 11 (NEI scale); and
a central corneal fluorescein staining value in the range of 1 to 3 (NEI scale).

2.59 A method of treating keratoconjunctivitis sicca (dry eye disease) comprising a step of topically administering an ophthalmic composition comprising 0.1% (w/v) cyclosporine dissolved in 1-(perfluorobutyl)pentane to an eye of a patient, wherein the patient has a total ocular surface disease index (OSDI) score of equal or greater than 45, and wherein the patient has at least one eye with:
a total corneal fluorescein staining score at least equal or higher than 11 (NEI scale);
a central corneal fluorescein staining value in the range of 1 to 3 (NEI scale); and
a total lissamine green conjunctival staining score in the range of 2 to 6.

2.60 A method of treating keratoconjunctivitis sicca (dry eye disease) comprising a step of topically administering an ophthalmic composition comprising 0.1% (w/v) cyclosporine dissolved in 1-(perfluorobutyl)pentane to an eye of a patient, wherein the patient has a total ocular surface disease index (OSDI) score of equal or greater than 45, and wherein the patient has at least one eye with:
a total corneal fluorescein staining score at least equal or higher than 11 (NEI scale);
a central corneal fluorescein staining value in the range of 1 to 3 (NEI scale);
a total lissamine green conjunctival staining score in the range of 2 to 6; and
an unanesthetized Schirmer's test score in the range of 4 to 6 mm.

2.61 Method 2.58 to 2.60, wherein the central corneal fluorescein staining value is about 3 (NEI scale).

2.62 Method 2.59 to 2.61, wherein the lissamine green conjunctival staining score is in the range of 3 to 5.

2.63 Method 2.60 to 2.62, wherein the unanesthetized Schirmer's test score is about 5 mm.

2.64 Method 2.57 to 2.63, wherein the patient has a total ocular surface disease index (OSDI) score of equal or greater than 55.

2.65 Method 2.49 to 2.64, wherein the patient has the total corneal fluorescein staining score, the central corneal fluorescein staining value, the lissamine green conjunctival staining score, and/or the unanesthetized Schirmer's test score with the specified values in both eyes.

In a third aspect, the present invention provides for the following items:

3.1 An ophthalmic composition comprising 0.1% (w/v) cyclosporine dissolved in 1-(perfluorobutyl) pentane for use in:
a) a method of treating and/or ameliorating the symptoms associated with keratoconjunctivitis sicca (dry eyes), wherein the symptoms are dryness (severity of dryness) and blurred vision;
and/or
b) a method of treating and/or ameliorating the awareness of symptoms of dry eyes and the frequency of dryness, preferably wherein the symptoms of dry eyes are selected from dryness, sticky feeling, burning/stinging, foreign body sensation, itching, blurred vision, sensitivity to light, and pain in the eyes of a patient.

3.2 The composition for use of 3.1, wherein the composition is topically administered to the eye of a patient.

3.3 The composition for use according to 3.1 or 3.2, wherein the dryness (severity of dryness), the blurred vision, the frequency of dryness and the awareness of symptoms of dry eyes are determined on a visual analog scale (VAS) on a scale of 0% to 100%, wherein for frequency of dryness and awareness of dry eyes symptoms the scale of 0% to 100% is the percentage of time dryness and dry eyes symptoms are experienced by a patient and wherein for dryness and blurred vision the scale of 0% to 100% is the percentage level of discomfort experienced by a patient.

3.4 The composition for use of any one of the preceding items, wherein the composition comprises up to about 1.0% (w/w) ethanol.

3.5 The composition for use of any one of the preceding items, wherein the composition consists of about 0.1% (w/v) cyclosporine, 1-perfluorobutylpentane (F4H5) and up to about 1.0% (w/w) ethanol.

3.6 The composition for use of any of the preceding items, wherein the ophthalmic composition is administered to the surface of the cornea and/or conjunctiva in the form of a liquid drop.

3.7 The composition for use in any of the preceding items, wherein the composition is administered as a single drop having a volume of about 8 to 11 μL, preferably of about 8 to 10 μL.

3.8 The composition for use of any of the preceding items, wherein the composition is administered in a dose of a single drop per eye in volume of about 8 to 10 μL.

3.9 The composition for use according to any one of the preceding claims, wherein the composition is administered as a single drop having a volume of about 10 μl.

3.10 The ophthalmic composition for use of any one of the preceding items, wherein the composition is administered twice per day per eye.

3.11 The composition for use in any of the preceding items, wherein the composition is administered in a dose of a single drop per eye twice per day in net volume of about 16-20 μL.

3.12 The composition for use according to any one of the preceding items, wherein the dry eye disease is aqueous-deficient dry eye disease.

3.13 The composition for use according to any of the preceding items, wherein the dry eye disease is evaporative dry eye disease.

3.14 The composition for use in according to any of the preceding items, wherein the patient is non-responsive, or insufficiently responsive, to treatment with aqueous ophthalmic eye drop compositions.

3.15 The composition for use of any of the preceding items, wherein the time interval between topical administration of the composition to the eye or eye surface of a first dose and a second dose is at least 4 hours, or at least 6 hours, or at least 12 hours.

3.16 The composition for use of any of the preceding items, wherein the duration of the treatment is for at least 2 weeks, or at least 4 weeks, or at least 6 weeks, or at least 8 weeks, or at least 12 weeks.

3.17 The composition for use of any of the preceding items wherein the patient is a human patient.

3.18 The composition for use of any of the preceding items, wherein the patient is a female patient.

3.19 The composition for use of any of the preceding items, wherein the patient is a male patient.

3.20 The composition for use of any of the preceding items, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

3.21 The composition for use of any of the preceding items, wherein the patient suffers from a co-morbidity, for example, conjunctivitis, stye, chalazion, blepharitis, ectropion, eyelid laxity, eyelid edema, eyelid dermatitis, punctate keratopathy, or ocular allergies, or any combination thereof.

3.22 The composition for use of any of the preceding items, wherein the patient suffers from keratoconjunctivitis sicca which is caused by treatment of a co-morbidity, for example, treatment with any one or more of: isotretinoin, sedatives, diuretics, tricyclic antidepressants, antihypertensives, anticholinergics, oral contraceptives, antihistamine, nasal decongestants, beta-adrenergic antagonists, phenothiazines, atropine opiates (e.g., morphine), optionally wherein any such treatment is concurrent or previous, and further optionally, wherein any such treatment is systemic (e.g., oral or parenteral).

3.23 The composition for use of any of the preceding items, wherein the patient suffers from keratoconjunctivitis sicca which is caused by ocular surgical intervention, for example, corneal surgery, refractive surgery, LASIK surgery, cataract surgery, optionally wherein any such ocular surgery is concurrent or previous.

3.24 The composition for use of any of the preceding items, wherein the patient is concomitantly under treatment with another topical ophthalmic medication, for example, an antibiotic, antifungal, corticosteroid, another immunosuppressant, sympathomimetic, anesthetic, antihistamine, or any combination thereof.

3.25 The composition for use of any of the preceding items, wherein the patient is a contact lens wearer.

3.26 The composition for use of any of the preceding items, wherein the patient was unresponsive or insufficiently responsive to previous treatment for keratoconjunctivitis sicca (dry eye disease).

3.27 The composition for use in 3.26, wherein said previous treatment comprise one or more of the following treatment methods: topical aqueous immunosuppressant administration (e.g., topical aqueous ciclosporin), topical corticosteroid administration, or topical aqueous artificial tears administration.

3.28 The composition for use of any of the preceding items, wherein the patient has at least one eye with any one, or combination of criteria (e.g. signs of dry eye disease) selected from the group consisting of:
  i. A total lissamine green conjunctival score (sum of temporal and nasal regions) of 2 according to the Oxford scale;
  ii. a total corneal fluorescein staining (NEI scale) of 10 (i.e. sum of inferior, superior, central, nasal and temporal regions); and
  iii. an unanesthetized Schirmer's Test score between 1 mm and 10 mm;
  and/or
  wherein the patient has a total ocular surface disease index score (OSDI) of equal or greater than 20.

3.29 The composition for use according to any of the preceding items, wherein the patient has a total ocular surface disease index score (OSDI) of equal or greater than 45.

3.30 The composition for use according to any of the preceding items, wherein the patient has a total ocular surface disease index score (OSDI) of equal or greater than 55.

3.31 The composition for use according to item 3.28 to 3.30, wherein the patient has at least one eye (i.e. the same eye) which meets all of criteria (i), (ii), and (iii).
3.32 The composition for use of any of the preceding items, wherein the patient has a history of keratoconjunctivitis sicca (dry eye disease) in one or both eyes for at least six months.
3.33 The composition for use of any of the preceding items, wherein the composition is effective in reducing one or more signs and/or symptoms of keratoconjunctivitis sicca (dry eye disease), preferably wherein the signs and/or symptoms is selected from ocular surface damage.
3.34 The composition for use of any of the preceding items, wherein the composition is effective in reducing one or more signs and/or symptoms of keratoconjunctivitis sicca (dry eye disease) within 2 weeks, or within 4 weeks, or within 8 weeks after first administration of the composition.
3.35 The composition for use in in any of the preceding items, wherein the composition is effective in reducing ocular surface damage.
3.36 The composition for use according to item 3.35, wherein the ocular surface damage is selected from the group consisting of:
  i. surface damage of the total corneal region;
  ii. surface damage of the central corneal region;
  iii. surface damage of the nasal corneal region;
  iv. surface damage of the temporal corneal region;
  v. surface damage of the inferior corneal region; and
  vi. combinations thereof.
3.37 The composition for use of item 3.36, wherein the ocular surface damage is selected from ocular surface damage in the central corneal region and ocular surface damage of the inferior corneal region.
3.38 The composition for use of item 3.35 to 3.37 wherein the reduction of ocular surface damage is determined by corneal fluorescein staining (NEI scale).
3.39 The composition for use in item 3.38, wherein the corneal fluorescein staining method is selected from the group consisting of:
  iv. total corneal fluorescein staining;
  v. central corneal fluorescein staining;
  vi. nasal corneal fluorescein staining;
  vii. temporal fluorescein staining;
  viii. inferior corneal fluorescein staining; and
  ix. any combination thereof.
3.40 The composition for use of any of the preceding items, wherein the composition is effective in reducing the frequency of dryness and/or the awareness of dry eye symptoms and/or the severity of dryness and any combination thereof.
3.41 The composition for use of item 3.40, wherein the composition is effective in reducing the frequency of dryness and/or the awareness of dry eye symptoms and/or the severity of dryness, or any combination thereof, within 2 weeks after start of treatment, or within 4 weeks after start of treatment.
3.42 The composition for use of item 3.40 or 3.41 wherein the composition is effective in reducing the frequency of dryness and/or the severity of dryness by at least 25%, preferably by at least 30% after two weeks or after four weeks or after 8 weeks or after 12 weeks of treatment.
3.43 The composition for use of item 3.40 to 3.42, wherein the composition is effective in reducing the severity of dryness and/or the frequency of dryness by at least 25% in more than at least 20% of patients undergoing treatment after two weeks of treatment; or in more than 30% of patients undergoing treatment after four weeks of treatment; or in more than at least 35% of patients under going treatment after eight weeks of treatment.
3.44 The composition for use of items 3.40 to 3.43, wherein the effectiveness of the composition for use is determined by visual analog scale (VAS) testing on a scale of 0 to 100%, wherein frequency of dryness and awareness of dry eye symptoms are measured on a scale of 0 to 100% as the percentage of time said symptom(s) is experienced by a patient and wherein the severity of dryness is measured on a scale of 0 to 100% as the percentage level of discomfort experienced by the patient.
3.45 The composition for use of any preceding item, wherein the method of treatment comprises reducing ocular surface damage, e.g. ocular surface damage of the cornea, or ocular surface damage selected from i. surface damage of the total corneal region; ii. surface damage of the central corneal region; iii. surface damage of the nasal corneal region; iv. surface damage of the temporal corneal region; v. surface damage of the inferior corneal region; and vi. combinations thereof.
3.46 The composition for use of item 3.45, wherein the ocular surface damage is selected from ocular surface damage in the central corneal region and ocular surface damage of the inferior corneal region.
3.47 The composition for use of item 3.45 to 3.46 wherein the ocular surface damage is determined by corneal fluorescein staining (NEI scale).
3.48 The composition for use of any of the preceding items, wherein patient has at least one eye with any one or combination of criteria selected from the group consisting of:
  a total corneal fluorescein staining value in the range of 10 to 15, preferably 10 to 13 (NEI scale);
  a central corneal fluorescein staining value in the range of 1 to 3 (NEI scale); preferably 2 to 3 (NEI scale);
  a total lissamine green conjunctival staining score in the range of 2 to 6, preferably 3 to 5;
  an unanesthetized Schirmer's test score in the range of 2 to 8 mm;
  a total OSDI score in the range of 25 to 64, preferably 30 to 64.
3.49 The composition for use of any of the preceding items, wherein the patient has an unanesthetized Schirmer's Test score in the range of 3 to 7 mm, preferably in the range of 4 to 6 mm, more preferably of about 5 mm.
3.50 The composition for use of any of the preceding items, wherein the composition is effective in reducing in a patient the total corneal fluorescein staining score (sum of inferior, superior, central, nasal, and temporal staining scores; NEI scale), by at least 3 grades after 4 weeks of treatment, preferably in at least 50% of the patients undergoing treatment.
3.51 The composition for use of any preceding items, wherein the composition is effective in reducing the central corneal fluorescein staining score in a patient by at least 1 grade after four weeks of treatment, preferably in at least 50% of the patients undergoing treatment.
3.52 The composition for use of any preceding items, wherein the composition is effective in reducing the conjunctival lissamine green staining (Oxford scale) in a patient by at least 2 grades after four weeks or after twelve weeks of treatment, preferably in at least 30% of the patients undergoing treatment after four weeks of treatment or preferably in at least 50% of the patients after twelve weeks of treatment.

3.53 The composition for use of any of the preceding items, wherein the patient does not suffer from meibomian gland dysfunction and/or blepharitis.

3.54 The composition for use of any of the preceding items, wherein the patient has at least one eye with a total corneal fluorescein staining score at least equal or higher than 11 (NEI scale).

3.55 The composition for use of any of the preceding items, wherein the patient has at least one eye with a central corneal fluorescein staining value in the range of 1 to 3 (NEI scale).

3.56 The composition for use of any of the preceding items, wherein the patient has at least one eye with a total lissamine green conjunctival staining score in the range of 2 to 6.

3.57 The composition for use of any of the preceding items, wherein the patient has at least one eye with an unanesthetized Schirmer's test score in the range of 4 to 6 mm.

3.58 The composition for use of any of the preceding items, wherein the central corneal fluorescein staining value is about 3 (NEI scale).

3.59 The composition for use of any of the preceding items, wherein the lissamine green conjunctival staining score is in the range of 3 to 5.

3.60 The composition for use of any of the preceding items, wherein the unanesthetized Schirmer's test score is about 5 mm.

3.61 An ophthalmic composition comprising 0.1% (w/v) cyclosporine dissolved in 1-(perfluorobutyl)pentane for use in:
   a) a method of treating and/or ameliorating the symptoms associated with keratoconjunctivitis sicca (dry eyes), wherein the symptoms are dryness (severity of dryness) and blurred vision;
   and/or
   b) a method of treating and/or ameliorating the awareness of symptoms of dry eyes and the frequency of dryness, preferably wherein the symptoms of dry eyes are selected from dryness, sticky feeling, burning/stinging, foreign body sensation, itching, blurred vision, sensitivity to light, and pain in the eyes of a patient; wherein the composition is topically administered to the eye of a patient, and wherein the patient has at least one eye with a total corneal fluorescein staining score at least equal or higher than 11 (NEI scale).

3.62 The composition for use of item 3.61, wherein the patient has at least one eye with a central corneal fluorescein staining value in the range of 1 to 3 (NEI scale).

3.63 The composition for use of item 3.61 or 3.62, wherein the patient has at least one eye with a total lissamine green conjunctival staining score in the range of 2 to 6.

3.64 The composition for use of any one of items 3.61 to 3.63, wherein the patient has at least one eye with an unanesthetized Schirmer's test score in the range of 4 to 6 mm.

3.65 The composition for use of any one of items 3.62 to 3.64, wherein the central corneal fluorescein staining value is about 3 (NEI scale).

3.66 The composition for use of any one of items 3.63 to 3.65, wherein the lissamine green conjunctival staining score is in the range of 3 to 5.

3.67 The composition for use of any one of items 3.64 to 3.66, wherein the unanesthetized Schirmer's test score is about 5 mm.

3.68 The composition for use of any one of items 3.61 to 3.67, wherein the patient has a total ocular surface disease index score (OSDI) of equal or greater than 45.

3.69 The composition for use of any one of items 3.61 to 3.68, wherein the patient has a total ocular surface disease index score (OSDI) of equal or greater than 55.

3.70 The composition for use in any one of items 3.54 to 3.69, wherein the patient has the total corneal fluorescein staining score, the central corneal fluorescein staining value, the lissamine green conjunctival staining score, and/or the unanesthetized Schirmer's test score with the specified values in both eyes.

In a fourth aspect, the present invention provides for the following method:

4.1 A method of treating and/or ameliorating the symptoms associated with keratoconjunctivitis sicca (dry eyes) wherein the symptoms are dryness (severity of dryness) and blurred vision, and wherein the method comprises administering an ophthalmic composition comprising 0.1% (w/v) cyclosporine dissolved in 1-(perfluorobutyl)pentane to an eye of a patient.

4.2 Method 4.1 and/or a method of treating and/or ameliorating the awareness of symptoms of dry eyes and the frequency of dryness, preferably wherein the symptoms of dry eye are selected from dryness, sticky feeling, burning/stinging, foreign body sensation, itching, blurred vision, sensitivity to light, and pain, wherein said method comprises administering an ophthalmic composition comprising 0.1% (w/v) cyclosporine dissolved in 1-(perfluorobutyl)pentane to an eye of a patient.

4.3 Method 4.1 or 4.2, wherein the composition is topically administered to the eye of a patient.

4.4 Method 4.1 to 4.3, wherein the dryness (severity of dryness), the blurred vision, the frequency of dryness and the awareness of symptoms of dry eyes are determined on a visual analog scale (VAS) on a scale of 0% to 100%, wherein for frequency of dryness and awareness of dry eyes symptoms the scale of 0% to 100% is the percentage of time dryness and dry eyes symptoms are experienced by a patient and wherein for dryness and blurred vision the scale of 0% to 100% is the percentage level of discomfort experienced by a patient.

4.5 Any preceding method, wherein the composition comprises up to about 1.0% (w/w) ethanol.

4.6 Any preceding method, wherein the composition consists of about 0.1% (w/v) cyclosporine, 1-(perfluorobutyl) pentane (F4H5) and up to about 1.0% (w/w) ethanol.

4.7 Any preceding method, wherein the ophthalmic composition is administered to the surface of the cornea and/or conjunctiva in the form of a liquid drop.

4.8 Any preceding method, wherein the composition is administered as a single drop having a volume of about 8 to 11 µL, preferably of about 8 to 10 µL.

4.9 Any preceding method, wherein the composition is administered in a dose of a single drop per eye in volume of about 8 to 10 µL.

4.10 Any preceding method, wherein the composition is administered as a single drop having a volume of about 10 µl.

4.11 Any preceding method, wherein the composition is administered twice per day per eye.

4.12 Any preceding method, wherein the composition is administered in a dose of a single drop per eye twice per day in net volume of about 16-20 µL.

4.13 Any preceding method, wherein the dry eye disease is aqueous-deficient dry eye disease.

4.14 Any preceding method, wherein the dry eye disease is evaporative dry eye disease.

4.15 Any preceding method, wherein the patient is non-responsive, or insufficiently responsive, to treatment with aqueous ophthalmic eye drop compositions.

4.16 Any preceding method, wherein the time interval between topical administration of the composition to the eye or eye surface of a first dose and a second dose is at least 4 hours, or at least 6 hours, or at least 12 hours.

4.17 Any preceding method, wherein the duration of the treatment is for at least 2 weeks, or at least 4 weeks, or at least 6 weeks, or at least 8 weeks, or at least 12 weeks.

4.18 Any preceding method, wherein the patient is a human patient.

4.19 Any preceding method, wherein the patient is a female patient.

4.20 Any preceding method, wherein the patient is a male patient.

4.21 Any preceding method, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

4.22 Any preceding method, wherein the patient suffers from a co-morbidity, for example, conjunctivitis, stye, chalazion, blepharitis, ectropion, eyelid laxity, eyelid edema, eyelid dermatitis, punctate keratopathy, or ocular allergies, or any combination thereof.

4.23 Any preceding method, wherein the patient suffers from keratoconjunctivitis sicca which is caused by treatment of a co-morbidity, for example, treatment with any one or more of: isotretinoin, sedatives, diuretics, tricyclic antidepressants, antihypertensives, anticholinergics, oral contraceptives, antihistamine, nasal decongestants, beta-adrenergic antagonists, phenothiazines, atropine opiates (e.g., morphine), optionally wherein any such treatment is concurrent or previous, and further optionally, wherein any such treatment is systemic (e.g., oral or parenteral).

4.24 Any preceding method, wherein the patient suffers from keratoconjunctivitis sicca which is caused by ocular surgical intervention, for example, corneal surgery, refractive surgery, LASIK surgery, cataract surgery, optionally wherein any such ocular surgery is concurrent or previous.

4.25 Any preceding method, wherein the patient is concomitantly under treatment with another topical ophthalmic medication, for example, an antibiotic, antifungal, corticosteroid, another immunosuppressant, sympathomimetic, anesthetic, antihistamine, or any combination thereof.

4.26 Any preceding method, wherein the patient is a contact lens wearer.

4.27 Any preceding method, wherein the patient was unresponsive or insufficiently responsive to previous treatment for keratoconjunctivitis sicca (dry eye disease).

4.28 Method 4.27, wherein said previous treatment comprises one or more of the following treatment methods: topical aqueous immunosuppressant administration (e.g., topical aqueous ciclosporin), topical corticosteroid administration, or topical aqueous artificial tears administration.

4.29 Any preceding method, wherein the patient has at least one eye with any one, or combination of criteria (e.g. signs of dry eye disease) selected from the group consisting of:
  i. A total lissamine green conjunctival score (sum of temporal and nasal regions) of ≥2 according to the Oxford scale;
  ii. a total corneal fluorescein staining (NEI scale) of ≥10 (i.e. sum of inferior, superior, central, nasal and temporal regions); and
  iii. an unanesthetized Schirmer's Test score between 1 mm and 10 mm;
  and/or
  wherein the patient has a total ocular surface disease index score (OSDI) of equal or greater than 20.

4.30 Any preceding method, wherein the patient has a total ocular surface disease index score (OSDI) of equal or greater than 45.

4.31 Any preceding method, wherein the patient has a total ocular surface disease index score (OSDI) of equal or greater than 55.

4.32 Method 4.29 to 4.31, wherein the patient has at least one eye (i.e. the same eye) which meets all of criteria (i), (ii), and (iii).

4.33 Any preceding method, wherein the patient has a history of keratoconjunctivitis sicca (dry eye disease) in one or both eyes for at least six months.

4.34 Any preceding method, wherein the composition is effective in reducing one or more signs and/or symptoms of keratoconjunctivitis sicca (dry eye disease), preferably wherein the signs and/or symptoms is selected from ocular surface damage 4.35 Any preceding method, wherein the composition is effective in reducing one or more signs and/or symptoms of keratoconjunctivitis sicca (dry eye disease) within 2 weeks, or within 4 weeks, or within 8 weeks after first administration of the composition.

4.36 Any preceding method, wherein the composition is effective in reducing ocular surface damage.

4.37 Method 4.36, wherein the ocular surface damage is selected from the group consisting of:
  i. surface damage of the total corneal region;
  ii. surface damage of the central corneal region;
  iii. surface damage of the nasal corneal region;
  iv. surface damage of the temporal corneal region;
  v. surface damage of the inferior corneal region; and
  vi. combinations thereof.

4.38 Method 4.37, wherein the ocular surface damage is selected from ocular surface damage in the central corneal region and ocular surface damage of the inferior corneal region.

4.39 Method 4.36 to 4.38 wherein the reduction of ocular surface damage is determined by corneal fluorescein staining (NEI scale).

4.40 Method 4.39, wherein the corneal fluorescein staining method is selected from the group consisting of:
  iv. total corneal fluorescein staining;
  v. central corneal fluorescein staining;
  vi. nasal corneal fluorescein staining;
  vii. temporal fluorescein staining;
  viii. inferior corneal fluorescein staining; and
  ix. any combination thereof.

4.41 Any preceding method, wherein the composition is effective in reducing the frequency of dryness and/or the awareness of dry eye symptoms and/or the severity of dryness and any combination thereof.

4.42 Method 4.41, wherein the composition is effective in reducing the frequency of dryness and/or the awareness of dry eye symptoms and/or the severity of dryness, or any combination thereof, within 2 weeks after start of treatment, or within 4 weeks after start of treatment.

4.43 Method 4.41 or 4.42 wherein the composition is effective in reducing the frequency of dryness and/or the severity of dryness by at least 25% after two weeks or after four weeks or after 8 weeks or after 12 weeks of treatment.

4.44 Method 4.41 to 3.43, wherein the composition is effective in reducing the severity of dryness and/or the frequency of dryness by at least 25% in more than 20% of patients undergoing treatment after two weeks of treatment; or in more than 30% of patients undergoing treatment after four weeks of treatment; or in more than 35% of patients undergoing treatment after eight weeks of treatment.

4.45 Method 4.41 to 4.44, wherein the effectiveness of the composition for use is determined by visual analog scale (VAS) testing on a scale of 0 to 100%, wherein frequency of dryness and awareness of dry eye symptoms are measured on a scale of 0 to 100% as the percentage of time said symptom(s) is experienced by a patient and wherein the severity of dryness is measured on a scale of 0 to 100% as the percentage level of discomfort experienced by the patient.

4.46 Any preceding method, wherein the method of treatment comprises reducing ocular surface damage, e.g. ocular surface damage of the cornea, or ocular surface damage selected from i. surface damage of the total corneal region; ii. surface damage of the central corneal region; iii. surface damage of the nasal corneal region; iv. surface damage of the temporal corneal region; v. surface damage of the inferior corneal region; and vi. combinations thereof.

4.47 Method 4.46, wherein the ocular surface damage is selected from ocular surface damage in the central corneal region and ocular surface damage of the inferior corneal region.

4.48 Method 4.46 to 4.47 wherein the ocular surface damage is determined by corneal fluorescein staining (NEI scale).

4.49 Any preceding method, wherein the patient has at least one eye with any one or combination of criteria selected from the group consisting of:
 a total corneal fluorescein staining value in the range of 10 to 15, preferably 10 to 13 (NEI scale);
 a central corneal fluorescein staining value in the range of 1 to 3 (NEI scale);
 preferably 2 to 3 (NEI scale);
 a total lissamine green conjunctival staining score in the range of 2 to 6, preferably 3 to 5;
 an unanesthetized Schirmer's test score in the range of 2 to 8 mm;
 a total OSDI score in the range of 25 to 64, preferably 30 to 64.

4.50 Any preceding method, in which the patient does not suffer from blepharitis and/or meibomian gland dysfunction.

4.51 Any preceding method, wherein the patient has an unanesthetized Schirmer's Test score in the range of 3 to 7 mm, preferably in the range of 4 to 6 mm, more preferably of about 5 mm.

4.52 Any preceding method, wherein the method is effective in reducing in a patient the total corneal fluorescein staining score (sum of inferior, superior, central, nasal, and temporal staining scores; NEI scale), by at least 3 grades after 4 weeks of treatment, preferably in at least 50% of the patients undergoing treatment.

4.53 Any preceding method, wherein the method is effective in reducing the central corneal fluorescein staining score in a patient by at least 1 grade after four weeks of treatment, preferably in at least 50% of the patients undergoing treatment.

4.54 Any preceding method, wherein the method is effective in reducing the conjunctival lissamine green staining (Oxford scale) in a patient by at least 2 grades after four weeks or after twelve weeks of treatment, preferably in at least 30% of the patients undergoing treatment after four weeks of treatment or preferably in at least 50% of the patients after twelve weeks of treatment.

4.55 Any preceding method, wherein the patient has at least one eye with a total corneal fluorescein staining score at least equal or higher than 11 (NEI scale).

4.56 Any preceding method, wherein the patient has at least one eye with a central corneal fluorescein staining value in the range of 1 to 3 (NEI scale).

4.57 Any preceding method, wherein the patient has at least one eye with a total lissamine green conjunctival staining score in the range of 2 to 6.

4.58 Any preceding method, wherein the patient has at least one eye with an unanesthetized Schirmer's test score in the range of 4 to 6 mm.

4.59 Any preceding method, wherein the central corneal fluorescein staining value is about 3 (NEI scale).

4.60 Any preceding method, wherein the lissamine green conjunctival staining score is in the range of 3 to 5.

4.61 Any preceding method, wherein the unanesthetized Schirmer's test score is about 5 mm.

4.62 A method of treating and/or ameliorating the symptoms associated with keratoconjunctivitis sicca (dry eyes) wherein the symptoms are dryness (severity of dryness) and blurred vision, wherein the method comprises administering an ophthalmic composition comprising 0.1% (w/v) cyclosporine dissolved in 1-(perfluorobutyl)pentane to an eye of a patient, and wherein the patient has at least one eye with a total corneal fluorescein staining score at least equal or higher than 11 (NEI scale).

4.63 Method 4.62 and/or a method of treating and/or ameliorating the awareness of symptoms of dry eyes and the frequency of dryness, preferably wherein the symptoms of dry eye are selected from dryness, sticky feeling, burning/stinging, foreign body sensation, itching, blurred vision, sensitivity to light, and pain, wherein said method comprises administering an ophthalmic composition comprising 0.1% (w/v) cyclosporine dissolved in 1-(perfluorobutyl)pentane to an eye of a patient, and wherein the patient has at least one eye with a total corneal fluorescein staining score at least equal or higher than 11 (NEI scale).

4.64 Method 4.62 or 4.63, wherein the patient has at least one eye with a central corneal fluorescein staining value in the range of 1 to 3 (NEI scale).

4.65 Method 4.62 to 4.64, wherein the patient has at least one eye with a total lissamine green conjunctival staining score in the range of 2 to 6.

4.66 Method 4.62 to 4.65, wherein the patient has at least one eye with an unanesthetized Schirmer's test score in the range of 4 to 6 mm.

4.67 Method 4.64 to 4.66, wherein the central corneal fluorescein staining value is about 3 (NEI scale).

4.68 Method 4.65 to 4.67, wherein the lissamine green conjunctival staining score is in the range of 3 to 5.

4.69 Method 4.66 to 4.68, wherein the unanesthetized Schirmer's test score is about 5 mm.

4.70 Method 4.62 to 4.69, wherein the patient has a total ocular surface disease index score (OSDI) of equal or greater than 45.

4.71 Method 4.62 to 4.70, wherein the patient has a total ocular surface disease index score (OSDI) of equal or greater than 55.

4.72 Method 4.55 to 4.71, wherein the patient has the total corneal fluorescein staining score, the central corneal fluorescein staining value, the lissamine green conjunctival staining score, and/or the unanesthetized Schirmer's test score with the specified values in both eyes.

In another aspect, the present invention provides for the following method:

5.1 A method for predicting the improvement of visual function in a subject suffering from dry eye disease (keratoconjunctivitis sicca) and characterized by a total corneal fluorescein staining score in the range of 10 to 15 (NEI scale) at baseline, wherein a decrease of the total corneal fluorescein staining score (NEI scale) by 3 or more units is indicative for improvement of visual function.

5.2 The method according to item 5.1, wherein the improvement of visual function comprises improvement in the number of words read per minute in an international reading speed texts (IReST).

5.3 The method according to item 5.1 or 5.2, wherein the improvement of visual function comprises improvement with regard to blurred vision, reading, driving at night, working with a computer, working at an automatic teller machine, reading at low contrast and reading at low print size.

5.4 The method according to any preceding items, wherein the subject is undergoing treatment that is effective in reducing ocular surface damage.

5.5 The method according to item 5.4, wherein the treatment is selected from a) an ophthalmic composition comprising cyclosporine at a concentration of from 0.05 to 0.1% (w/v) or b) an ophthalmic composition comprising lifitegrast.

5.6 The method according to any preceding items, wherein the treatment is a composition comprising 0.1% (w/v) cyclosporine dissolved in 1-perfluorobutyl-pentane and up to about 1% (w/w) ethanol.

5.7 The method according to item 5.6, wherein the composition is administered in a dose of a single drop per eye in volume of about 8 to 12 μL.

5.8 The method according to item 5.7, wherein the composition is administered as a single drop per eye having a volume of about 10-12 μl.

5.9 The method according to any of items 5.6-5.8, wherein the composition is administered twice per day per eye.

5.10 Any preceding method, wherein the subject has at least one eye with a total corneal fluorescein staining score at least equal or higher than 11 (NEI scale).

5.11 Any preceding method, wherein the subject has at least one eye with a central corneal fluorescein staining value in the range of 1 to 3 (NEI scale).

5.12 Any preceding method, wherein the subject has at least one eye with a total lissamine green conjunctival staining score in the range of 2 to 6.

5.13 Any preceding method, wherein the subject has at least one eye with an unanesthetized Schirmer's test score in the range of 4 to 6 mm.

5.14 Any preceding method, wherein the central corneal fluorescein staining value is about 3 (NEI scale).

5.15 Any preceding method, wherein the lissamine green conjunctival staining score is in the range of 3 to 5.

5.16 Any preceding method, wherein the unanesthetized Schirmer's test score is about 5 mm.

5.17 A method for predicting the improvement of visual function in a subject suffering from dry eye disease (keratoconjunctivitis sicca) and characterized by a total corneal fluorescein staining score at least equal or higher than 11 (NEI scale) at baseline, wherein a decrease of the total corneal fluorescein staining score (NEI scale) by 3 or more units is indicative for improvement of visual function.

5.18 Method 5.17, wherein the subject has at least one eye with a central corneal fluorescein staining value in the range of 1 to 3 (NEI scale).

5.19 Method 5.17 or 5.18, wherein the subject has at least one eye with a total lissamine green conjunctival staining score in the range of 2 to 6.

5.20 Method 5.17 to 5.19, wherein the subject has at least one eye with an unanesthetized Schirmer's test score in the range of 4 to 6 mm.

5.21 Method 5.18 to 5.20, wherein the central corneal fluorescein staining value is about 3 (NEI scale).

5.22 Method 5.19 to 5.21, wherein the lissamine green conjunctival staining score is in the range of 3 to 5.

5.23 Method 5.20 to 5.22, wherein the unanesthetized Schirmer's test score is about 5 mm.

5.24 Method 5.17 to 5.23, wherein the subject has a total ocular surface disease index score (OSDI) of equal or greater than 45.

5.25 Method 5.17 to 5.24, wherein the subject has a total ocular surface disease index score (OSDI) of equal or greater than 55.

5.26 Method 5.10 to 5.25, wherein the patient has the total corneal fluorescein staining score, the central corneal fluorescein staining value, the lissamine green conjunctival staining score, and/or the unanesthetized Schirmer's test score with the specified values in both eyes.

In a further aspect, the present invention provides for an ophthalmic composition for use in a method of increasing tear production volume in a subject, wherein the composition comprises 0.1% w/v cyclosporine dissolved in 1-(perfluorobutyl)pentane. Said method may comprise a step of topically administering the composition to an eye of a subject, for example to the surface of the eye (e.g. the surface of the cornea and/or conjunctiva). The composition may be administered in the form of a single (i.e. one) liquid drop per dose. Preferably, the drop volume of said administered dose is between about 8 to 10 μL. In one embodiment of said aspect, the composition may be administered twice a day per eye of the subject. The composition according to said aspect may comprise of about 0.1% w/v cyclosporine dissolved in 1-(perfluorobutyl)pentane, and optionally, up to about 1.0% w/w of ethanol. In another embodiment according to this aspect, the composition for use in said method of increasing tear production volume in a subject may be a solution consisting of about 0.1% w/v cyclosporine dissolved in 1-(perfluorobutyl)pentane and about 1.0% w/w ethanol. In yet a further embodiment according to this aspect, the composition is a solution consisting of about 0.1% w/v cyclosporin dissolved in 1-(perfluorobutyl)pentane.

The ophthalmic composition for use according to this aspect and any one of its embodiments above may be used in a method of increasing tear production volume in a subject, wherein the subject's tear production is suppressed, or presumed to be suppressed because of ocular inflammation associated with keratoconjunctivitis sicca. Tear suppression, such as due to ocular inflammation associated with keratoconjunctivitis sicca in the subject may for example be determined in a subject based on any one or combination of the methods as described herein used to assay dry eye disease signs and symptoms, for example Schirmer type I test or corneal fluorescein staining, or patient questionnaire.

In another aspect, the present invention provides for an ophthalmic composition for use in a method of treating xerophthalmia, wherein the composition comprises 0.1% w/v cyclosporine dissolved in 1-(perfluorobutyl)pentane. Preferably said treatment method increases tear production in the subject. The method according to said aspect may comprise a step of topically administering the composition to an eye of a subject, for example to the surface of the eye (e.g. the cornea and/or conjunctiva). The composition may be administered in the form of a single liquid drop per dose; in an embodiment, the volume of the administered drop is between about 8 to 10 µL. The composition may be administered twice daily (two times per day) per eye of the subject. In one embodiment, the composition according to said aspect may comprise of about 0.1% w/v cyclosporine dissolved in 1-(perfluorobutyl)pentane, and optionally, up to about 1.0% w/w of ethanol.

In another embodiment according to this aspect, the composition for use in said method of treating xerophthalmia, optionally wherein the method increases tear production in a subject, is a solution consisting of about 0.1% w/v cyclosporine dissolved in 1-(perfluorobutyl)pentane and about 1.0% w/w ethanol. In an alternative embodiment according to this aspect, the composition is a solution consisting of 0.1% w/v cyclosporin dissolved in 1-(perfluorobutyl)pentane.

Damage to the cornea and associated tissues is prevalent in patients with dry eye disease, in particular those with moderate to severe, or severe dry eye disease. The tear film, with its lipid, aqueous and mucin layers normally provides a protective barrier to corneal tissue and corneal epithelium and has a wetting function i.e. prevents drying/desiccation. It acts as a conduit for the provision of oxygen and nutrients to the corneal epithelial cells, as well as removal of any potential pathogens, debris and waste products. In patients with dry eye disease, the tear film is typically unstable or disrupted (for example, as a result of reduced aqueous secretion or increased evaporation of the tear film, or reduced secretion of mucin or lipids) and consequently, the corneal tissue, and conjunctiva may become less protected and vulnerable and/or prone to damage and deterioration.

The severity of ocular surface damage which may be characterized by, for example punctate disruption of the corneal epithelium or surface disruption of the bulbar conjunctiva, may be assessed by corneal and conjunctival staining measurements, for example such as described herein, i.e. fluorescein staining (NEI scale) and lissamine green staining (Oxford scale), which highlight and stain in particular, dead or damaged corneal and conjunctival cells. Particularly, central corneal fluorescein staining (NEI scale), which assays the central corneal area (as compared to the peripheral corneal area including inferior, superior, nasal, and temporal regions of the cornea), reflects ocular surface damage that impacts visual function impairment.

As used herein, the term 'corneal staining' or 'total corneal staining', optionally in conjunction with the mention of fluorescein, or a dye that is suitable or adapted for staining of the cornea, refers to staining observed as a sum in respect of all regions of the cornea, i.e. the inferior, superior, central, temporal, and nasal regions of the cornea. The term 'central corneal staining' or the like (i.e. with specific corneal region prefacing) and optionally in conjunction with the dye used for staining, such as fluorescein, refers specifically to staining observed only in the specified anatomical region.

As used herein, the term 'conjunctival staining' or 'total conjunctival staining', optionally in conjunction with the mention of fluorescein or a dye suitable or adapted for staining of the cornea, refers to staining observed as a sum in respect of all regions of the conjunctivitis, i.e. the temporal and nasal regions of the conjunctivitis. Where the term is used specifying the specific conjunctival region (e.g. nasal conjunctiva staining), optionally in conjunction with mention of the dye used for staining, such as lissamine green, it is to be understood that this refers specifically to staining observed in said region.

In one embodiment, the ophthalmic composition for any one of the uses according to the invention may be used to treat and reduce the signs of dry eye diseases, in particular treat or reduce ocular surface damage, such as corneal damage and/or conjunctival damage, in a subject suffering from dry eye disease. In one embodiment, said subject to be treated may have ocular surface damage of the cornea, and have a total corneal fluorescein staining score of at least equal to, or greater than 10 (≥10), the score being the sum of scores obtained for inferior, superior, central, nasal, and temporal regions of the cornea, based on the NEI grading scale of 0-3. In another embodiment, the subject may have a total corneal fluorescein staining score of at least equal to, or greater than 11, prior to commencement of treatment, optionally wherein the subject has a total OSDI score of equal to or greater than 45, or equal or greater than 55.

In another embodiment, the ophthalmic composition according to any one of the uses according to the invention may be used to reduce ocular surface damage, such as corneal damage and/or conjunctival damage, in a subject suffering from dry eye disease. In one embodiment, said subject may have a central corneal fluorescein staining score of at least equal to, or greater than 2 (≥2), based on the NEI grading scale of 0-3. In another embodiment, said subject may in addition also have a total lissamine green conjunctival staining score (sum of temporal and nasal regions), based on the Oxford scale, of at least equal to, or greater than 2 (i.e. ≥2).

In one embodiment, the invention relates to an ophthalmic composition for use in treating i.e. reducing ocular surface damage in a subject suffering from dry eye disease, wherein said subject has a total OSDI score of equal, or greater than 45, wherein the composition comprises about 0.1% (w/v) cyclosporine dissolved in 1-(perfluorobutyl)pentane, and optionally up to about 1.0% (w/w) of ethanol; wherein the composition is administered topically twice daily, one drop per eye at a drop volume of about 8 to 10 µL. In another specific embodiment, such use may be for the treatment e.g. reduction of corneal surface damage, in particular reduction of ocular surface damage of the central corneal region and/or the inferior corneal region.

In a further embodiment, said ophthalmic composition may be used in the effective treatment of patients with dry eye disease with signs of corneal ocular surface damage (e.g. with total corneal staining scores (NEI scale) of at least 11) wherein the composition is administered twice daily. Said composition may be topically administered as a single drop per dose and per eye, said drop having a volume of about 10 µL.

In another embodiment, the present disclosure relates to an ophthalmic composition comprising 0.1% (w/v) cyclosporine dissolved in 1-(perfluorobutyl)pentane for use in: a) a method of treating and/or ameliorating the symptoms associated with keratoconjunctivitis sicca (dry eye disease), wherein the symptoms are dryness, and blurred vision; and/or b) for use in a method of treating and/or ameliorating the awareness of symptoms of dry eye disease and the frequency of dryness.

Optionally, the method of treatment according to said embodiment comprises topical administration twice daily of a single drop of the composition per eye, further optionally at a drop volume of about 8 to 10 µL. In yet a further embodiment, said composition may consist of 0.1% (w/v) cyclosporine dissolved in 1-(perfluorobutyl)pentane and optionally up to 1.0% (w/w) of ethanol.

As used herein, the term 'severity of dryness' may be used interchangeably with the term (ocular) 'dryness', which refers to the symptomatic ocular sensation of dryness which may be experienced by patients with keratoconjunctivitis sicca (dry eye disease).

It has been found that the composition for use as defined above is surprisingly efficacious in treating, i.e. reducing the degree of severity in particular in dry eye symptoms selected from dryness and blurred vision. As noted above, dryness refers to the ocular sensation of dryness, and is the first question of the VAS questionnaire as described below. Blurred vision may refer to for example a certain degree of impaired vision, e.g. objects/text appear to subjects with blurred vision to be less well-defined or unclear, or may appear partially obscured. These symptoms may contribute to overall visual impairment or difficulties, which can have a negative effect on the subject's performance in functional tasks where visual performance and acuity may be essential. Thus a positive and in particular early impact in terms of alleviating and reducing these symptoms in subjects can be particularly beneficial, in terms of improving quality of vision and providing relief, and in particular in subjects for which the discomfort level of these symptoms is very high and frequent.

As well as a reduction in severity of dryness and blurred vision, the present composition according to the invention has also been found to be effective in reducing the overall degree of frequency of dryness. A reduction in frequency in which dryness, is experienced by a subject, and/or reduction in a subject's overall awareness of dry eye symptoms, may also be beneficial in terms of improving overall quality of vision and would allow the subject undertake activities, which may be previously may be severely limited due to frequent irritation or distraction due to constant awareness or occurrence of dry eye symptoms.

The amelioration of these symptoms may be based on, and determined by application of the visual analog scale (VAS) eye dryness test, wherein the patients are assessed over the course of treatment in respect of said symptoms on a scale of 0-100% level of discomfort, as well as on a scale of 0 to 100%, the percentage of time in which they are aware of, or experience (i.e. frequency) the symptoms in their eyes.

In one embodiment, the compositions for any of the uses of the present invention are effective in improving by at least 25% a reduction in the severity of dryness (e.g. ocular dryness) and/or the frequency of dryness experienced by a patient or subject as described herein. In another embodiment, the composition is effective in providing at least a 25% reduction in severity of dryness and frequency of dryness within 2 weeks of commencement of the treatment. In another embodiment, the composition is effective in providing at least a 25% reduction in severity of dryness and frequency of dryness within 2 weeks of commencement of the treatment in at least 25% of the subjects undergoing the treatment. In a further embodiment, the treatment is effective in providing at least 25% reduction in severity of dryness and/or frequency of dryness, within 4 weeks of commencement i.e. start of the treatment in at least 30% of the subjects undergoing the treatment. The reduction may be determined by comparison of VAS scoring for each or combination of the above symptoms with initial baseline scores obtained prior to treatment.

In further embodiments, the method of treating keratoconjunctivitis sicca (dry eye disease) may comprise the topical administration of a composition according to the invention to an eye, or both eyes of a patient and treating or ameliorating the frequency of dryness and/or awareness of the symptoms associated with dry eye disease (e.g. symptoms selected from dryness, sticky feeling, burning/stinging, foreign body sensation, itching, blurred vision, sensitivity to light, and pain), wherein said treatment comprises an effective reduction of the frequency of dryness or awareness of dry eye symptoms in general, of at least 25%, within 2, or within 4 weeks after the start of treatment.

Optionally, the ophthalmic composition and dosage thereof as described herein may be used for treating patients or subjects who are not responsive, or who are insufficiently responsive to treatment with aqueous artificial tears.

Artificial tears, also known as lubricating eye drops or tear substitutes are used for relief and treatment of the symptoms of dry eye disease, and which normally may be obtained over the counter (OTC). These are normally aqueous-based compositions, in the form of solutions, but also in the form of gels or ointments which function by adding moisture to the eyes, and usually may comprise lubricating agents (e.g. hydroxypropyl methyl cellulose (HPMC), carbomethylcellulose (CMC), polyvinyl alcohol, liquid polyols such as propylene glycol, polyethylene glycol) and may contain additives which promote healing (e.g. hyaluronic acid) or mimic electrolyte composition of natural tear film, or which promote retention (e.g. gelling agents such as carbomers) of the composition on the eye surface.

In an embodiment, the ophthalmic compositions for any one of the uses according to the invention may be used to treat patients with persisting dry eye disease symptoms and associated conditions even following a treatment period with only aqueous artificial tears over a period of at least 2 weeks, or at least 1 month, or at least about 6 months.

A dose of a composition for any one of the uses according to the present invention and as described in any one of the embodiments herein is topically administered in the form of a (i.e. one) single drop to an eye of a subject. The drop may be administered to the surface of the eye, preferably to any surface region or tissue of the eye that is accessible to topical administration or instillation, for example to the cornea or conjunctiva. The single drop of the composition may be instilled directly onto a surface of the eye, such as the corneal surface of the eye, or alternatively into a space i.e. sac or pocket formed by gently pulling down of the lower eyelid of an eye.

As used herein, the term 'administration to an eye' or 'per eye' refers to the administration of a given dose, e.g. a single dose, of a ophthalmic composition according to the invention to an individual eye of a subject. The therapy of the dry eye disease and dry eye disease associated conditions as described herein however, should be understood as being not limited to the treatment of a single eye in a subject, but as being also inclusive of a therapy involving the administration of compositions according to the present invention to each i.e. both eyes of a subject which are affected by the dry eye condition.

In an embodiment of the invention, the ophthalmic compositions for any of the uses described herein are administered at a dose of a single drop two times a day per eye. Thus, a patient undergoing treatment for both eyes in accordance with such dosing scheme would receive a total of two drops for each eye on each day of a given treatment period.

Where the ophthalmic composition is administered more than once per day to each eye, for example two times daily per eye, in a further embodiment, the time interval between topical administration of the composition to the eye or eye surface of the first dose and the second dose may be at least 4 hours, or at least 6 hours, or at least 12 hours.

In a further embodiment, the ophthalmic compositions for any of the uses of the present invention are administered over a treatment period of at least 1 month (four weeks), and more at least 3 months (12 weeks). In another embodiment, the ophthalmic compositions for any of the uses of the present invention may be administered on a continuous basis while dry eye disease symptoms and indicators persist.

In other embodiments, the ophthalmic compositions for any of the uses in accordance with the invention may comprise up to about 1.0% (w/w) of ethanol.

As used herein, the term "up to about" or "up to" used in context of a parameter, such as presently in relation to the amount of ethanol in the composition, refers to any value of the parameter greater than zero and up to, and inclusive of, the defined parameter. For example, an amount of "up to about 1.0% (w/w) of ethanol" should be understood as including any value greater than zero ranging up to and including the value of 1.0% (w/w) of ethanol, and would include, for example, values such as 0.01%, 0.05%, 0.1%, 0.2%, 0.3%, 0.4%, 0.5% 0.6%, 0.7, 0.8, 0.9, 0.95%, 0.99% (w/w) of ethanol, taking into account any degree of variability usually observed in measuring or determining this parameter, using the standard techniques and equipment known in the relevant field.

In one embodiment of the invention, the compositions for the therapeutic uses as described herein may consist essentially of about 0.1% (w/v) cyclosporine dissolved in 1-(perfluorobutyl)pentane, and optionally about 1.0% (w/w) of ethanol.

In another embodiment, the compositions as described herein are essentially free of ethanol, in which the composition consists essentially only of cyclosporine in an amount as described in any of the embodiments described herein dissolved in 1-(perfluorobutyl)pentane.

The absence of an organic co-solvent such as ethanol may offer the advantages of a simpler two component formulation compared to a three component formulation additionally comprising a co-solvent such as ethanol. The further inclusion, of even one additional composition component may add complexity in terms of factors such as cost, manufacturing, handling, packaging, and also patient compliance.

In preferred embodiments of the invention, the compositions for any of the uses as described herein may preferably comprise, or consist of:
about 0.1% (w/v) of cyclosporine dissolved in 1-(perfluorobutyl)pentane and about 0.5% (w/w) ethanol, or
about 0.1% (w/v) cyclosporine dissolved in 1-(perfluorobutyl)pentane and about 1.0% (w/w) ethanol, or
about 0.1% (w/v) cyclosporine dissolved in 1-(perfluorobutyl)pentane.

The compositions for any of the uses of the invention are preferably provided as a clear solution, wherein the cyclosporine is fully dissolved and in solution in the 1-(perfluorobutyl)pentane (at room temperature conditions i.e. between 15 to 25° C.). If ethanol is included, said compositions are also provided as a clear solution of cyclosporine dissolved and in solution in 1-(perfluorobutyl)pentane and the ethanol. In one embodiment, the compositions are provided in sterile form.

In another embodiment, the ophthalmic compositions for any one of the uses according to the present invention are substantially free of water and/or substantially free of a preservative. As understood herein, the term 'substantially free', or alternatively 'essentially free' in reference to a composition constituent refers to the presence of said constituent in no more than trace amounts and that if present in trace amounts the constituent provides no technical contribution to the composition.

Preferably, the ophthalmic compositions for any one of the uses according to the present invention are substantially free of water, substantially free of a preservative and are effective in inhibiting microbial growth.

In another embodiment, the ophthalmic compositions for any one of the uses according to the present invention are characterized by a remarkable wetting and spreading behaviour by which they can rapidly and effectively spread over the surface of the eye, such as the corneal and/or the conjunctival surface. Thus, a droplet (drop) of the ophthalmic compositions for any one of the uses according to the present invention when administered to the surface of the eye leads to rapid spreading of the compositions over the corneal and/or the conjunctival surface.

Preferably, the ophthalmic compositions for any one of the uses according to the present invention form small droplets (drops), in the range of about 8-10 μl, such as about 10 μL when administered from a drop dispenser.

In another preferred embodiment, the ophthalmic compositions for any one of the uses according to the present invention are characterized by the comparable low amount of cyclosporine administered in a single dose per eye, such as about 10 μg cyclosporine administered in a single dose per eye, or about 8 to 10 μg of cyclosporin administered in a single dose per eye.

As used herein, the term "consists" and related terms "consisting" or "consist" is to be understood as meaning that no other features, other than those prefaced by the term are present. In the context of the ophthalmic compositions as described herein, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g. 'essentially consisting of").

The use of an ophthalmic composition as described in any one of the above embodiments in the manufacture or preparation of a medicament or a medicine for the treatment of a subject in need thereof in relation to any one of preferred dry eye disease conditions described herein are also provided for in the context of the present invention. Further provided for within the context of the present invention, are also methods of treating subjects diagnosed with, and/or suffering from said dry eye disease conditions as described herein, wherein the methods may comprise the topical administration, such as by direct topical instillation to the eye, of any one of the defined compositions, preferably in any one of the described doses or amounts, and/or over any one of the defined periods for therapy.

Said treatment methods and compositions for therapeutic use are moreover preferably targeted towards human subjects or patients diagnosed and/or suffering dry eye disease.

In yet a further aspect, the invention provides also a kit comprising an ophthalmic composition for any one of the uses according to the invention and any of the embodiments described above. In an embodiment, the kit comprises a container for holding the ophthalmic composition and a drop dispenser adapted for administering about 8 to 10 µL, or about 10 µl volume of the composition per drop. The kit may also further comprise instructions for use, for examples in the form of a leaflet, packaging or other readable means, indicating use in accordance with any one of the uses or methods described herein.

As understood herein, the drop dispenser may be a dispenser or applicator means which may be mounted, fixed or connected to the container for holding the ophthalmic composition. Preferably, the drop dispenser is adapted for dispensing a single dose in the form of a single drop of the composition. More preferably, the drop dispenser is adapted for dispensing a single dose of about 8- to 10-µl volume, or is adapted for dispensing a single dose of about 10-µl volume.

The container for holding the ophthalmic composition as understood herein is preferably of a volume which may hold a single dose, but more preferably of a volume which may hold multiple or a plurality of doses of the composition.

The following examples serve to illustrate the invention, however should not to be understood as restricting the scope of the invention.

EXAMPLES

Example 1

Study Setup

A Phase 2b/3, multi-center, randomized, double-masked (vehicle)-controlled clinical study to assess the efficacy, and safety and of topical CyclASol® for treatment of the signs and symptoms of dry eye disease. The study is listed in clinicaltrials.gov under the number NCT03292809.

Subjects eligible to be randomized received one of the following treatments to dose with bilaterally BID for approximately 85 days (from Visit 1 to Visit 5):
1) CyclASol 0.1% Ophthalmic Solution (Cyclosporine A 0.1% solution)
2) Vehicle Ophthalmic Solution (F4H5)

CyclASol 0.1% Ophthalmic Solution is a clear ophthalmic solution of Cyclosporine A dissolved in 1-(perfluorobutyl)pentane. 1-(perfluorobutyl)pentane, which is commonly abbreviated F4H5 is used as the vehicle. The only other component in the formulation is ethanol 1.0% (w/w) as co-solvent. The administered dose of CyclASol, i.e. a single drop has a volume of about 8-10 µL.

A 14-day study-run-in period was used for subject selection before randomization. During this period, all subjects received Systane® Balance to dose with bilaterally BID.

The study involved 6 visits over the course of approximately 14 weeks:
Visit 0, –Day –14±2 days, Screening;
Visit 1, Day 1, Baseline/Randomization;
Visit 2, Day 15±1 days, 2-Week Follow-Up;
Visit 3, Day 29±2 days, 4-Week Follow-Up;
Visit 4, Day 57±2 days, 8-Week Follow-Up; and
Visit 5, Day 85±2 days, 12-Week Follow-Up and Study Exit.

Study Population

Patients included in the study had to fulfill following criteria:
(a) Be at least 18 years of age;
(b) Provide written informed consent;
(c) Have a subject reported history of Dry Eye Disease in both eyes for at least 180 days before Visit 0;
(d) Be currently using (within 30 days before Visit 0) over-the-counter (OTC) eye drops and/or artificial tears for dry eye symptoms at Visit 0;
(e) Have a total OSDI® score of ≥20 at Visit 0 and Visit 1;
(f) Have a total corneal fluorescein staining score of ≥10 (i.e. sum of inferior, superior, central, nasal, and temporal regions) according to the NEI scale at Visit 0 and Visit 1;
(g) Have a total lissamine green conjunctival score (sum of temporal and nasal regions) of ≥2 according to the Oxford scale at Visit 0 and Visit 1;
(h) Have an unanesthetized Schirmer's Test score between 1 mm and 10 mm inclusive at Visit 0 and Visit 1;
(i) Have at least one eye, the same eye, satisfy inclusion criteria f, g, and h; and
(j) Be able and willing to follow instructions and participate in all study assessments and visits.

Each subject must not:
a. Have any clinically significant slit-lamp findings at Visit 0 that require prescriptive medical treatment and/or in the opinion of the investigator may interfere with study parameters including trauma, Steven Johnson Syndrome, advanced epithelial basement membrane disease;
b. Have active blepharitis, meibomian gland dysfunction (MGD) or lid margin inflammation that required any topical or systemic antibiotics or topical steroids or other prescription medical treatment or treatment with hypochlorous acid wipes within last 30 days prior to Visit 0 or will require such treatment during the study. Any other therapy such as lid scrubs, lid wipes, warm compresses have to be stable within the last 30 days prior to Visit 0 and the subject should be willing to continue those therapies through the study;
c. Have abnormal lid anatomy (e.g. incomplete eyelid closure, entropion, or ectropion) or abnormal blinking;
d. Have Dry Eye Disease secondary to scarring from, for example, irradiation, alkali burns, cicatricial pemphigoid, or conjunctival goblet cell destruction (i.e. conjunctival goblet cell destruction because of vitamin A deficiency);
e. Have an ocular or periocular malignancy;
f. Have any corneal epithelial defect, or have in more than 2 of the 5 corneal regions >50% confluent corneal staining;
g. Have a history of herpetic keratitis;
h. Have active ocular allergies or ocular allergies that may become active during the study period;
i. Be diagnosed with an ongoing ocular or systemic infection (bacterial, viral, or fungal), including a fever, or be undergoing treatment with antibiotics at Visit 0 or Visit 1;
j. Have worn contact lenses within 90 days before Visit 0 or anticipate using contact lenses during the study;
k. Have used any eye drops, gels or scrubs within 2 hours before Visit 0 or Visit 1;
l. Have used topical Cyclosporine A (CsA) or Lifitegrast within 60 days before Visit 0;
m. Have participated in a previous CyclASol study (patients who were assigned to the Restasis treatment arm may enter the study);

n. Have had intraocular surgery or ocular laser surgery within 180 days before Visit 0, or have any planned ocular or eyelid surgeries during the study period;
o. Be a woman who is pregnant, nursing, or planning a pregnancy;
p. Be unwilling to submit a urine pregnancy test at Visit 0 and Visit 5 (or early termination visit) if of childbearing potential. Non-childbearing potential is defined as a woman who is permanently sterilized (i.e. has had a hysterectomy, bilateral tubal ligation, or bilateral oophorectomy), or is post-menopausal (i.e. without menses for 12 consecutive months);
q. Be a woman of childbearing potential who is not using an acceptable means of contraception. Acceptable methods of contraception include hormonal contraceptives (i.e. oral, implantable, injectable, or transdermal contraceptives), mechanical contraceptives (i.e. spermicide in conjunction with a barrier such as a diaphragm or a condom), intrauterine devices (IUD), or the surgical sterilization of the partner. For non-sexually active females, abstinence may be regarded as an adequate method of birth control; however, if the subject becomes sexually active during the study, she must agree to use adequate birth control as defined above for the remainder of the study;
r. Have an uncontrolled systemic disease;
s. Have a known allergy or sensitivity to the study drug or its components: Cyclosporine A (CsA) or semifluorinated alkanes (SFA);
t. Have active ocular or periocular rosacea or a pterygium;
u. Be currently enrolled in an investigational drug or device study or have used an investigational drug or device within 60 days before Visit 0;
v. Have used any topical antiglaucoma medications within 90 days before Visit 0;
w. Have used any topical ocular or facial steroids, or serum tears, or oral doxycycline, or oral tetracycline within 30 days before Visit 0;
x. Have used systemic steroids (including dermatological steroids with high potency or large treatment areas) or immunomodulating agents on a non-stable regimen within 90 days before Visit 0 or anticipate their use on a non-stable regimen during the study period;
y. Have used any oral medications known to cause ocular drying (e.g. antihistamines or antidepressants) on a non-stable regimen within 30 days before Visit 0 or anticipate non-stable use of oral ocular-drying medication during the study;
z. Have a corrected visual acuity greater than or equal to log MAR+0.7 as assessed by the Early Treatment of Diabetic Retinopathy Study (ETDRS) scale in either eye at Visit 0 or Visit 1;
aa. Have a condition or be in a situation (e.g. language barrier) which the investigator feels may put the subject at significant risk, may confound the study results, or may interfere with the subject's participation in the study significantly; or
bb. Have received or removed a punctal plug within 90 days before Visit 0 or anticipate the implant or removal of a punctal plug during the study.

The full analysis set of patients were, respectively, 162 for CyclASol 0.1% treatment and 166 for vehicle treatment.

At baseline, the CyclASol 0.1% group of patients had the following characteristic: a mean total corneal fluorescein staining NEI scale (SD) of 11.5 (1.26); a mean central corneal fluorescein staining NEI scale (SD) of 2 (0.51); a mean conjunctival staining of 4.1 (1.70); a mean total OSDI (SD) of 46.9 (16.73); a VAS severity of dryness (SD) of 68.5 (21.6); a mean Schirmer test score of 5.2 (2.83).

At baseline, the vehicle group of patients had the following characteristics: a mean total corneal fluorescein staining NEI scale (SD) of 11.5 (1.25); a mean central corneal fluorescein staining NEI scale (SD) of 2 (0.52); a mean conjunctival staining of 4.3 (1.66); a mean total OSDI (SD) of 47.1 (16.41); a VAS severity of dryness (SD) of 69.9 (20.5); a mean Schirmer test score of 5.1 (2.64).

Instructions for Use

Subjects were instructed to instill one drop of treatment 1) or 2) in each lower eyelid two times daily (in the morning and in the evening before bed).

Evaluation Criteria

At each visit during the treatment period, each subject was assessed in terms of treatment efficacy using tests including: corneal fluorescein staining (NEI Grading); conjunctival staining (Lissamine, Oxford grading), as well as subject symptom assessment questionnaires such as Ocular Surface Disease Index questionnaire (OSDI, ref. Schiffman R. M. et al 2000; 118:615-621.) and visual analogue scale (VAS).

The following efficacy measures were obtained during the study:

Primary Efficacy Measures

The following primary endpoints were tested in order using hierarchical fixed sequence testing:
1. Change from baseline in total Corneal fluorescein staining (NEI scale) at Day 29.
2. Change from baseline in Ocular Surface Disease Index (OSDI) at Day 29.

Key Secondary Efficacy Measures included:
Total Corneal fluorescein staining (NEI scale) and change from baseline to each measured post-baseline visit (other than Day 29)
Ocular Surface Disease Index (OSDI) and change from baseline to each measured post-baseline visit (other than Day 29)
Lead/Worst symptom assessment
Reading impairment score and change from baseline to each measured post-baseline visit
Unanesthetized Schirmer's Test and change from baseline to each measured post-baseline visit
Central and inferior corneal staining (NEI scale) and changes from baseline to each measured post-baseline visit Secondary Efficacy Measures:
Reading assessment and change from baseline to each measured post-baseline visit
Corneal fluorescein staining other sub-regions (NEI scale) and changes from baseline to each measured post-baseline visit
Ocular Surface Disease Index (OSDI) subtotal scores and changes from baseline to each measured post-baseline visit
Conjunctival lissamine green staining by region and total (Oxford scale) and changes from baseline to each measured post-baseline visit
Tear film break-up time (TFBUT) and change from baseline to each measured post-baseline visit
Visual analog scale (VAS) and changes from baseline for severity of: dryness, burning/stinging, sticky feeling, foreign body sensation, itching, blurred vision, sensitivity to light, pain and for awareness of dry eye symptoms and frequency of dryness to each measured post-baseline visit
InflammaDry® test (MMP-9) and change from baseline to each measured post-baseline visit Symptoms as recorded in subject diary to each measured post-baseline visit Corneal Staining For corneal staining (Sook Chun Y et al., Am J Ophthalmol. 2014 May; 157(5):1097-102), 5 µl of 2% preservative-free sodium fluorescein solution was instilled into the inferior conjunctival cul-de-sac of each eye. In order to achieve maximum fluorescence, the fluorescein staining is evaluated only after approximately 3-5 minutes after instillation. A Wratten #12 yellow filter was used to enhance the ability to grade fluorescein staining.

The staining was graded with the NEI Grading Scale (The National Eye Institute grading system), with only the cornea being graded. Corneal fluorescein staining scores were obtained for each of the inferior, superior, central, temporal, and nasal regions of the cornea based on a 0-3 scale, where a score of 0 means no staining is observed. The term "total corneal fluorescein staining total score" refers to a sum of scores from the inferior, superior, central, temporal, and nasal regions of the cornea.

Conjunctival Lissamine Green Staining

Conjunctival Lissamine Green Staining (Bron A. J. et al, Cornea. 2003; 22:640-650) was conducted by instillation of 10 µl of lissamine green solution into the inferior conjunctival cul-de-sac of a subject. After waiting for approximately 30 seconds the staining was evaluated. The subject was instructed to blink several times to distribute the lissamine green. The staining was graded with the Oxford Grading Scale. Herein, the lissamine staining is represented by punctate dots on a series of panels (A-E). Staining ranges from 0-5 for each panel and 0-10 for the total exposed inter-palpebral conjunctiva. Both nasal and temporal regions were graded separately. A score of 0 means no staining. Total conjunctival lissamine green staining scores were obtained, referring to the sum of scores from both temporal and nasal regions of the conjunctiva.

Ocular Surface Disease Index (OSDI)

Ocular Surface Disease Index (OSDI) (ref. Schiffman R M, et al., Arch Ophthalmol. 2000; 118:615-621) is a survey tool used for the assessment of symptoms of ocular irritation in dry eye disease and how they affect functioning related to vision. It is a 12-item questionnaire assessing dry eye symptoms and effects on vision-related function in the past week of a patient's life. The questionnaire has 3 subscales: ocular symptoms, vision-related function, and environmental triggers. Patients rate their responses on a 0 to 4 scale with 0 corresponding to "none of the time" and 4 corresponding to "all of the time." A final score is calculated which ranges from 0 to 100.

The questions assess dry eye symptoms experienced by the patient within past week including the following: sensitivity to light, gritty sensation, pain or sore eyes, blurriness, and poor vision; vision-related function, in terms of problems in: reading, driving at night, working on a computer or bank machine, watching television; and in terms of environmental factors or triggers i.e. discomfort during: windy conditions, places with low humidity, and areas with air condition. Subtotals are obtained for all the questions, as well as the total number of questions answered. The OSDI index is assessed based on a scale of 0 to 100, with higher scores representing a greater disability. The OSDI index is calculated from the sum of the scores multiplied by a factor of 25, over the total number of questions answered.

Visual Analog Scale (VAS)

Subjects were asked to rate their ocular symptoms (both eyes simultaneously) due to ocular dryness in a 10-item questionnaire and asked to place a vertical mark on the horizontal line starting at the value of 0%, corresponding to no discomfort, and ending at a value of 100%, corresponding to maximal discomfort, to indicate the level of discomfort. Subjects were asked about the each of following: dryness (corresponding to the first question in the VAS questionnaire, and also referred to in the text and in the graphs as severity of dryness), sticky feeling (question 2), burning/stinging (question 3), foreign body sensation (question 4), itching (question 5), blurred vision (question 6), sensitivity to light (question 7), and pain (question 8). Subjects were also asked about their awareness of their dry eye symptoms (question 9) and frequency of dryness (question 10), in terms of the percentage of time. For these two questions, the value of 0% corresponds to 'never' and a value of 100% corresponds to "all of the time". The assessment line length of the scale is 100 mm (10 cm), with grading provided at every 10 mm (suggesting 10%, 20%, etc).

A comparison may be made between the values indicated by the patient at each visit, compared to baseline values at Day 1 visit 1, to determine the effectiveness of treatment.

Schirmer's Test I (without Anesthesia)

Schirmer Tear Test I is performed according to the following procedure. Do not blot prior to the test. Using a sterile Tear Flo Schirmer test strip, a bend in the strip is made in line with the notch in the strip. The subject is instructed to gaze up and in. The Schirmer test strip is placed in the lower temporal lid margin of each eye such that the strip fits tightly. Subjects were instructed to close their eyes. After 5 minutes have elapsed, the Schirmer strip was removed. The length of the moistened area was recorded (mm) for each eye.

Tear Film Break-up Time (TFBUT)

The examiner instilled 5 µL of 2% preservative-free sodium fluorescein solution into the inferior conjunctival cul-de-sac of each eye. To thoroughly mix the fluorescein with the tear film, the subject was instructed to blink several times. In order to achieve maximum fluorescence, the examiner should wait approximately 30 seconds after instillation before evaluating TFBUT.

With the aid of a slit-lamp, the examiner monitored the integrity of the tear film, noting the time it takes to form micelles from the time that the eye is opened. TFBUT was measured in seconds using a stopwatch and a digital image recording system for the right eye followed by the left eye. A Wratten #12 yellow filter was used to enhance the ability to grade TFBUT.

For each eye, two measurements were taken and averaged unless the two measurements are >2 seconds apart and are each <10 seconds, in which case, a third measurement would be taken and the two closest of the three would be averaged. All values were recorded in the source document.

Study Results

Figure 2:
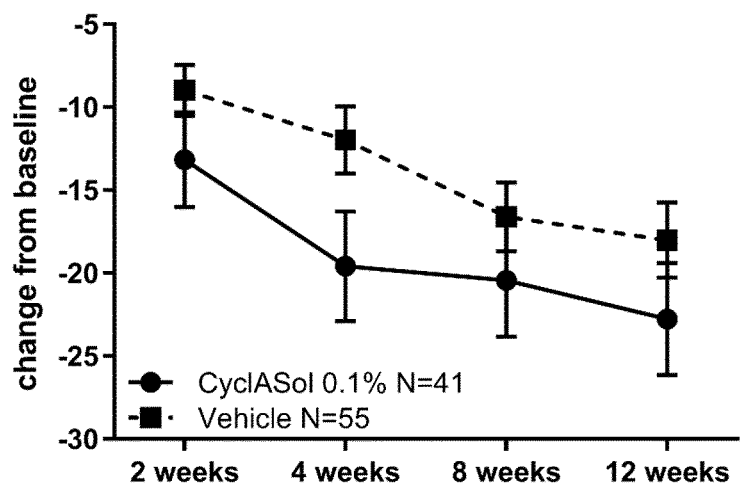
FIG. 2. Total ocular surface disease index (OSDI)—depicted is the change from baseline of the total OSDI score (mean) at 2 weeks, 4 weeks, 8 weeks and 12 weeks of treatment (two times per day) with vehicle (F4H5; N=55) and CyclASol 0.1% Ophthalmic Solution (clear ophthalmic solution of Cyclosporine A dissolved in 1-(perfluorobutyl)pentane, with 1.0% w/w ethanol; N=41), in subjects with a baseline total OSDI of 55 or greater.

It was observed that treatment with CyclASol in dry eye disease patients, having at baseline a total OSDI score of equal, or greater than 45 (≥45) obtained at the first visit (baseline score) was particularly effective (FIG. 1). It was observed that there was a significant change from the baseline of the total OSDI during the treatment. In particular, and compared with the vehicle, CyclASol also has a remarkable effect in the group of patients having a total OSDI ≥55 at baseline (FIG. 2).

It is also observed, compared to the general population of patients in the study, the mean change from baseline of total OSDI over the 12-week course of treatment with CyclASol was generally more significant for patients having an OSDI ≥45 or ≥55.

Figure 3:
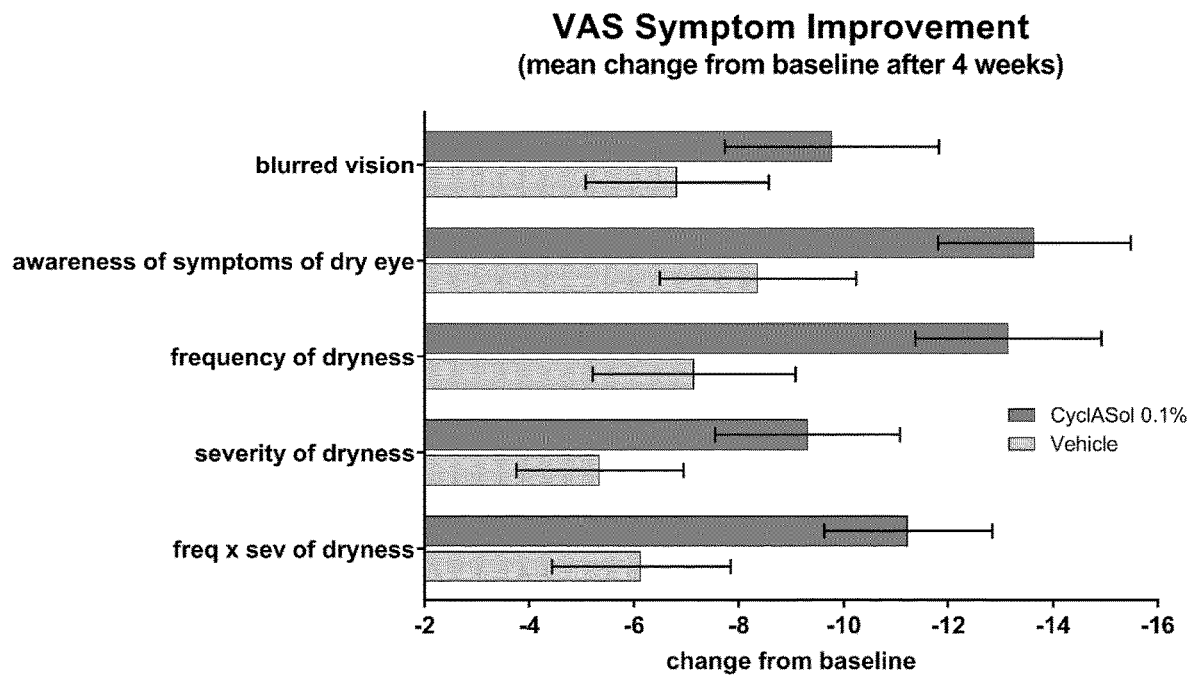
FIG. 3. VAS symptom improvements. Depicted is the mean change from baseline (Visit 1) after 4 weeks of the VAS score in study subjects administered (2 times per day) with vehicle (F4H5; N=165) and CyclASol 0.1% Ophthalmic Solution (N=160; clear ophthalmic solution of Cyclosporine A dissolved in 1-(perfluorobutyl)pentane, with 1.0% w/w ethanol) for: blurred vision, awareness of symptoms of dry eye, frequency of dryness, severity of dryness, and combined frequency and severity of dryness.
Figure 4:
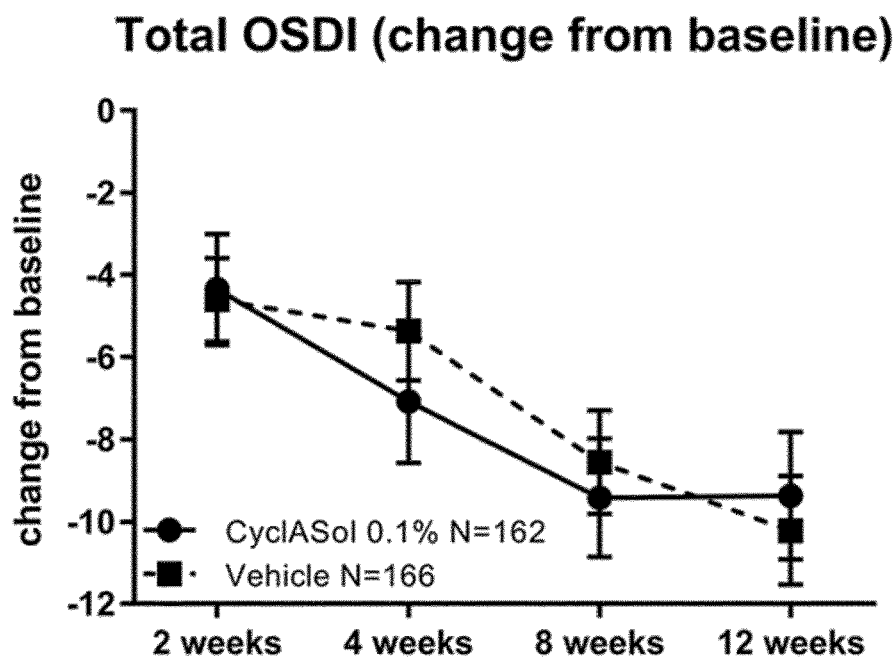
FIG. 4. Total ocular surface disease index (OSDI)—depicted is the change from baseline of the total OSDI score (mean) at 2 weeks, 4 weeks, 8 weeks and 12 weeks of treatment (2 times per day) with vehicle (F4H5; N=166) and CyclASol 0.1% Ophthalmic Solution (clear ophthalmic solution of Cyclosporine A dissolved in 1-(perfluorobutyl)pentane, with 1.0% w/w ethanol; N=162), for the entire population of subjects.

It was also found that compared to the vehicle, that the overall awareness and frequency of the symptoms of dry eye disease, assessed using the dry eye symptom visual analog scale (VAS) test, was significantly reduced, compared to baseline visit scoring, already after only 4 weeks duration of treatment with CyclASol (FIG. 3).

For the severity of dryness, which corresponds to the question relating to the symptom of "dryness" in the VAS questionnaire, it was also observed that the mean change from baseline was significant, at already 4 weeks of treatment in terms of a reduction in the level of severity of dryness. The baseline values for VAS severity of dryness were 68.5 and 69.9 for CyclASol 0.1% and vehicle, respectively.

Similarly, a reduction in the severity of blurred vision, which is assessed as part of the VAS (visual analog scale) test was also observed. At primary endpoint visit a statistically significant (p=0.02-0.03) symptoms improvement was shown for the symptoms shown in FIG. 3.

It was also found, that the proportion of patients in the study having at least 25% or higher improvement (compared to baseline visit values), in terms of a reduction in the severity of dryness as determined by the VAS test was higher for CyclASol at all visits compared to the vehicle. The proportion of patients with a response rate of 25% or higher from treatment with CyclASol, with respect to a reduction in severity of dryness, was about 26%, already at week 2 of the treatment. At 4 weeks, at 8 weeks and at 12 weeks, the percentage of patients with a response rate of 25% or higher, that is with an improvement of 25% or more, for the reduction in severity of dryness was observed to be 33% 37% and 39%, respectively. Similarly, it was observed that the responder rate for the reduction in the frequency of dryness experienced by the patients, in terms of patients having 25% or higher degree of improvement (compared to baseline visit values), as determined by the VAS testing, was also higher for the CyclASol treatment compared to the vehicle. The proportion of patients with a response rate of 25% or higher from treatment with CyclASol, with respect to a reduction in the frequency of dryness, was 24%, already at week 2 of the treatment. At 4 weeks, at 8 weeks and at 12 weeks, the percentage of patients with a response rate of 25% or higher for the reduction in frequency of dryness was observed to be 34%, 42% and 37%, respectively.

Figure 5:
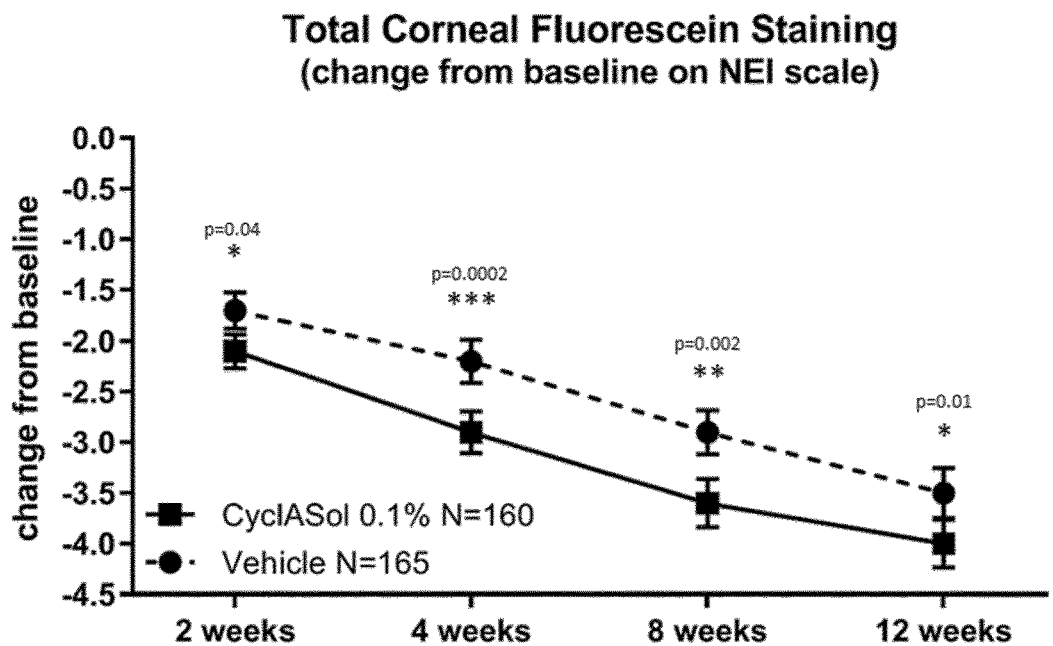
FIG. 5. Total corneal fluorescein staining (NEI scale)—depicted is the change from baseline of the total corneal fluorescein staining (mean) at 2 weeks, 4 weeks, 8 weeks and 12 weeks of treatment (2 times per day) with vehicle (F4H5; N=165) and CyclASol 0.1% Ophthalmic Solution (clear ophthalmic solution of Cyclosporine A dissolved in 1-(perfluorobutyl)pentane, with 1.0% w/w ethanol; N=160), for the entire population of subjects. Error bars show standard error of the mean (SEM).
Figure 6:
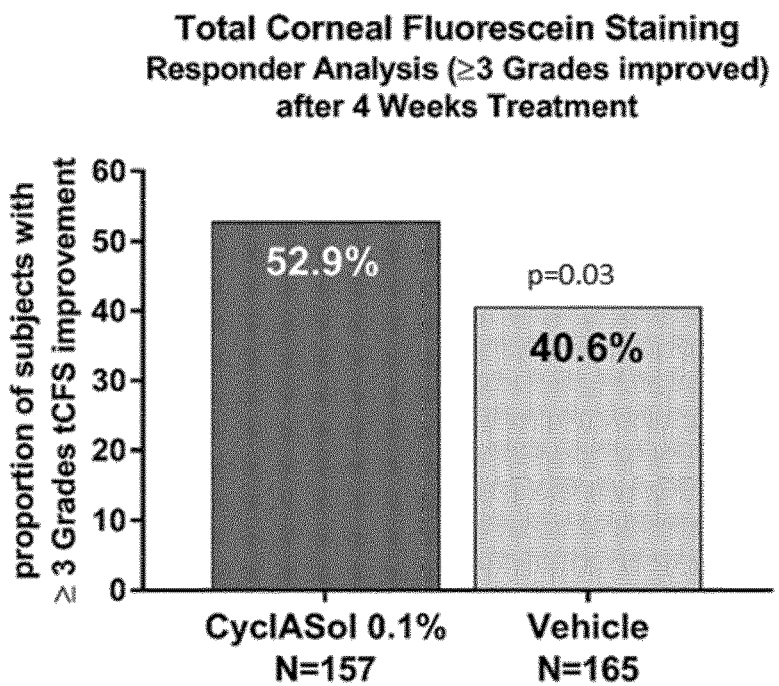
FIG. 6. Total corneal fluorescein staining responder analysis (≥3 grades improvement) after 4 weeks of treatment. Compared are the proportions of subjects, respectively treated with CyclASol 0.1% and vehicle, with a grades improvement in the total corneal fluorescein staining (tCFS).

The primary endpoint of the study at 4 weeks was met with high statistical and clinical significance, as shown in FIGS. 5 and 6. The onset of effect on the total corneal fluorescein staining was as early as two weeks and was sustained during the entire study duration (FIG. 5). The mean baseline value for tCFS for CyclASol 0.1% and vehicle was 11.5 for both groups. As shown in FIG. 6, more than 50% of all patients responded to CyclASol 0.1% with an improvement of ≥3 grades in total corneal fluorescein staining after 4 weeks of treatment.

Figure 7:
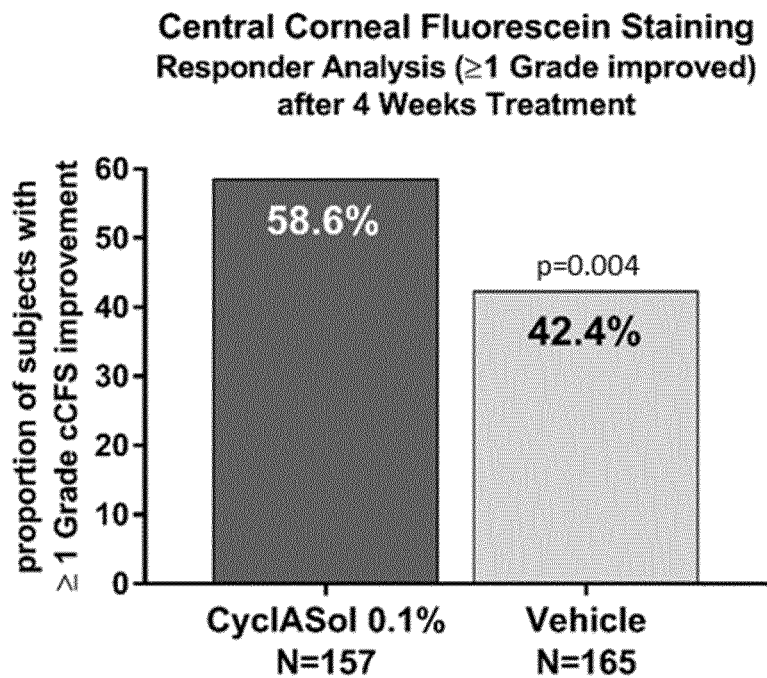
FIG. 7. Central corneal fluorescein staining (NEI scale) responder analysis (≥1 grade improvement) after 4 weeks of treatment. Compared are the proportions of subjects, respectively treated with CyclASol 0.1% and vehicle, with a 1 grade improvement in the central corneal fluorescein staining (cCFS).

The region of the cornea which benefited most of the CyclASol 0.1% treatment was the central area, which is the most important region for visual function. As shown in FIG. 7, an improvement in central corneal fluorescein staining ≥1 grade was obtained in 58.6% of the subjects undergoing CyclASol 0.1% treatment after 4 weeks treatment.

Figure 8:
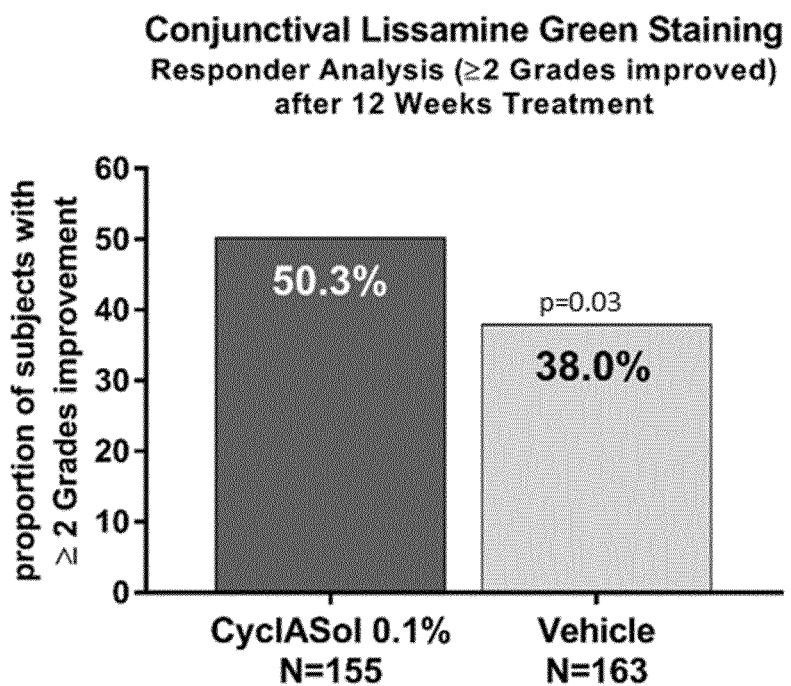
FIG. 8. Conjunctival lissamine green staining responder analysis (≥2 grades improvement) after 12 weeks of treatment. Compared are the proportions of subjects, respectively treated with CyclASol 0.1% and vehicle, with a ≥2 grades improvement in the conjunctival lissamine green staining.
Figure 9:
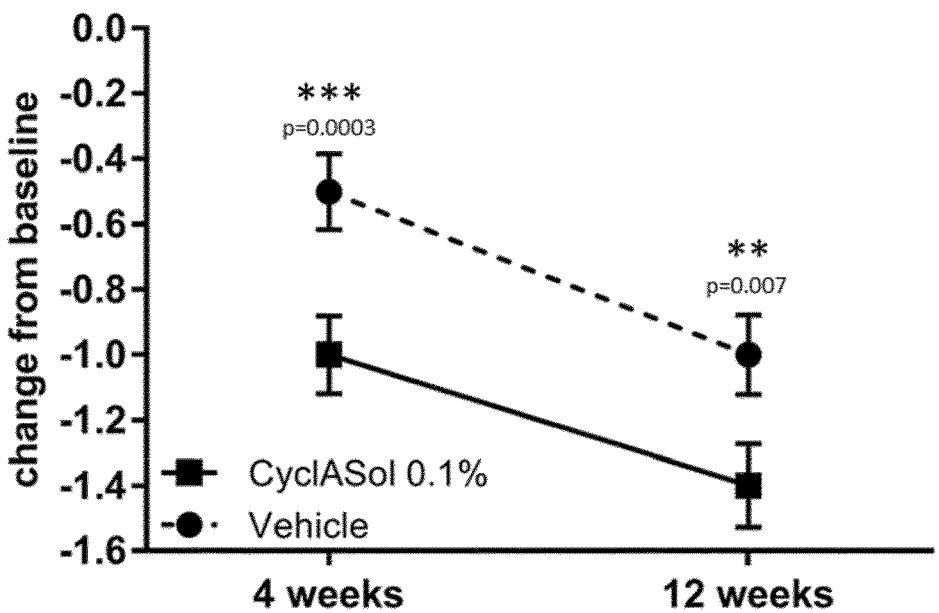
FIG. 9. Conjunctival lissamine green staining (change from baseline on Oxford scale)-depicted is the change from baseline of the conjunctival lissamine green staining value (mean) at 4 weeks and 12 weeks of treatment (2 times per day) with vehicle (F4H5) and CyclASol 0.1% Ophthalmic Solution (clear ophthalmic solution of Cyclosporine A dissolved in 1-(perfluorobutyl)pentane, with 1.0% w/w ethanol), for the entire population of subjects. Error bars show the standard error of the mean (SEM).
Figure 10:
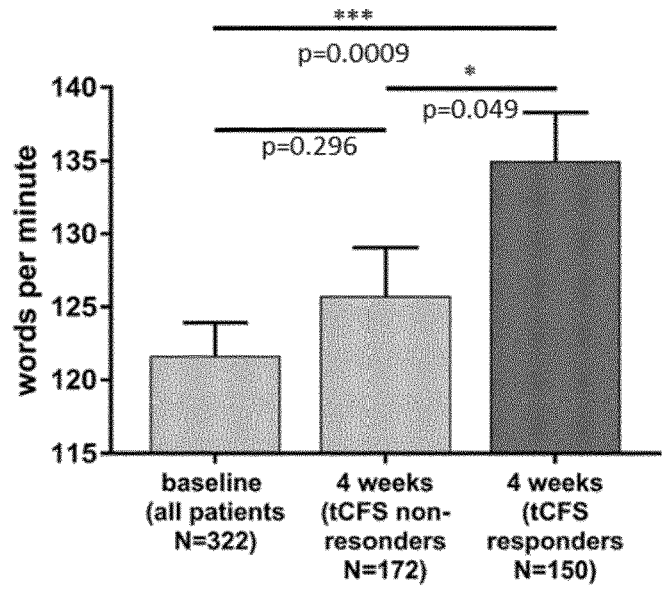
FIG. 10. International Reading Speed Texts (IResT) critical print size—depicted is the number of words read per minute for a) all the patients at baseline (N=322); b) the tCFS non responder group (N=172) after four weeks; and c) the tCFS responder group (N=150) after four weeks, wherein tCFS responders are subjects whose tCFS score decreased of 3 or more units (NEI) after four weeks.
Figure 11:
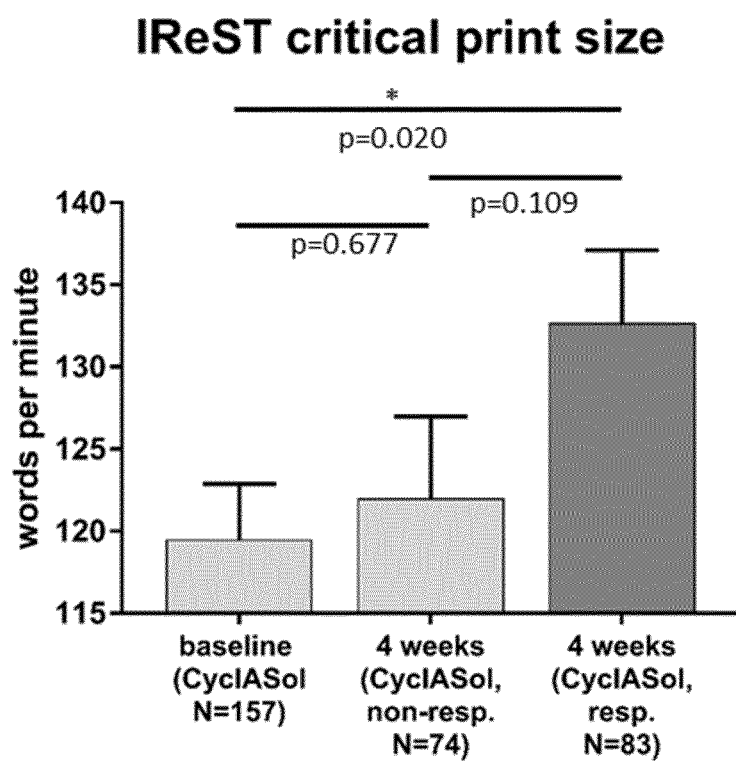
FIG. 11. International Reading Speed Texts (IResT) critical print size—depicted is the number of words read per minute for the CyclASol group of patients at baseline (N=157), the CyclASol tCFS non responders after four weeks (N=74) and the CyclASol tCFS responders after four weeks (N=83), respectively.

A high responder rate was obtained also on conjunctiva. In FIG. 8 it is shown that after 12 weeks treatment, 50.3% of the patients undergoing CyclASol 0.1% treatment improved of at least 2 grades in conjunctival lissamine green staining score, which is a sign relevant for ocular health. FIG. 9 shows the change from baseline of the conjunctival lissamine green staining in the two patients populations. The baseline values for the CyclASol 0.1% group and vehicle group are respectively 4.1 and 4.3.

The invention claimed is:

1. A method for improving symptoms of visual impairment or visual disturbance in a patient suffering from dry eye disease, wherein the patient is characterized by having at least one eye with a total ocular surface disease index score (OSDI) of equal or greater than 45 at baseline, wherein the method provides a reduction in the total corneal fluorescein staining score (NEI scale) by three or more units, and wherein the method comprises the step of administering to the eye of the patient a composition comprising 0.1% (w/v) cyclosporine dissolved in 1-(perfluorobutyl)-pentane and up to about 1% (w/w) ethanol; wherein said composition is administered twice per day per eye, at a dose of a single drop per eye of a volume of about 8 to 11 µL.

2. The method of claim 1, wherein the method comprises administering the composition for a period of at least four weeks.

3. The method of claim 1, wherein the method provides an improvement of any one or a combination of blurred vision, sensitivity to light, pain or sore eyes, poor vision, or problems in reading, driving at night, working on a computer or bank machine, and watching television.

4. The method of claim 1, wherein the composition is administered twice per day per eye, at a dose of a single drop per eye of a volume of about 8 to 10 µL.

5. The method of claim 1, wherein the patient has at least one eye with a total ocular surface disease index score (OSDI) of equal or greater than 55, and at least one eye with:
   (i) a total corneal fluorescein staining score of 11 or higher (NEI scale); or
   (ii) a central corneal fluorescein staining in the range of 1 to 3 (NEI scale); or
   (iii) a total lissamine green conjunctival staining score in the range of 2 to 6; or
   (iv) an unanesthetized Schirmer's test score in the range of 2 to 8 mm; or
   (v) any combination of (i) to (iv); or
   (vi) any combination of (i) to (iv), with the specified values in both eyes.

6. The method according to claim 5, wherein the central corneal fluorescein staining value is in the range of 2 to 3 (NEI scale).

7. The method according to claim 5, wherein the lissamine green conjunctival staining score is in the range of 3 to 5.

8. The method according to claim 1, wherein method provides a reduction in the total corneal fluorescein staining score (NEI scale) of at least 3 units within a treatment period of at least 8 weeks.

9. A method of treating and/or ameliorating the symptoms of dryness associated with dry eye disease in a patient in need thereof, wherein the method comprises topically administering an ophthalmic composition comprising 0.1% (w/v) cyclosporine dissolved in 1-(perfluorobutyl)pentane, and up to about 1.0% (w/w) ethanol, wherein the composition is administered in a dose of a single drop per eye in a volume of about 8 to 10 µL, twice per day per eye;
   wherein the composition is effective in reducing the frequency of the symptom of dryness and/or the severity of dryness within 4 weeks after start of treatment; and
   wherein the patient has at least one eye with a total ocular surface disease index score (OSDI) of equal or greater than 55; and wherein the patient has at least one eye with:

(i) a total corneal fluorescein staining score in the range of 10 to 15 (NEI scale); or
(ii) a central corneal fluorescein staining value in the range of 2 to 3 (NEI scale); or
(iii) a lissamine green conjunctival staining score in the range of 2 to 6; or
(iv) an unanesthetized Schirmer's test score in the range of 2 to 8 mm; or
(v) any combination of (i) to (iv); or
(vi) any combination of (i) to (iv), with the specified values in both eyes.

10. The method of claim 9, wherein the effectiveness in reduction in the frequency of dryness or the severity of dryness, or combination thereof is determined by visual analog scale (VAS) testing on a scale of 0 to 100%, wherein frequency of dryness and awareness of dry eye symptoms are measured on a scale of 0 to 100% as the percentage of time said symptom(s) is experienced by a patient and wherein the severity of dryness is measured on a scale of 0 to 100% as the percentage level of discomfort experienced by the patient.

11. The method of claim 9, wherein the composition is effective in reducing the frequency of dryness and/or the severity of dryness by at least 25%, after four weeks, as determined by visual analog scale (VAS) testing on a scale of 0 to 100%, wherein frequency of dryness and awareness of dry eye symptoms are measured on a scale of 0 to 100% as the percentage of time said symptom(s) is experienced by a patient and wherein the severity of dryness is measured on a scale of 0 to 100% as the percentage level of discomfort experienced by the patient.

12. The method of claim 9, wherein the method is effective in reducing in a patient the total corneal fluorescein staining score in at least one eye (sum of inferior, superior, central, nasal, and temporal staining scores; NEI scale), by at least 3 grades after 4 weeks of treatment.

13. The method of claim 9, wherein the dry eye disease is aqueous-deficient dry eye disease.

14. The method of claim 9, wherein the dry eye disease is evaporative dry eye disease.

15. The method of claim 9, wherein the patient is non-responsive, or insufficiently responsive, to treatment with aqueous ophthalmic eye drop compositions.

16. A method of treating dry eye disease, the method comprising the step of topically administering an ophthalmic composition comprising 0.1% (w/v) cyclosporine dissolved in 1-(perfluorobutyl)pentane and up to about 1.0% (w/w) ethanol to an eye of a patient; wherein the composition is administered twice per day per eye, and as a single drop having a volume of about 8 to 10 µL;
wherein the patient has at least one eye with a total ocular surface disease index (OSDI) score of equal or greater than 55; and wherein the patient has at least one eye with any one or combination of criteria selected from the group consisting of:
(i) a total corneal fluorescein staining score of 11 or higher (NEI scale);
(ii) a central corneal fluorescein staining value in the range of 2 to 3 (NEI scale);
(iii) a total lissamine green conjunctival staining score in the range of 2 to 6;
(iv) an unanesthetized Schirmer's test score in the range of 2 to 8 mm; and
(v) any one or combination of (i) to (iv); or
(vi) any combination of (i) to (iv), with the specified values in both eyes.

17. The method of claim 16, wherein treatment is effective in reducing ocular surface damage selected from ocular surface damage of the central corneal region and ocular surface damage of the inferior corneal region.

18. The method of claim 16, wherein the dry eye disease is aqueous-deficient dry eye disease.

19. The method of claim 16, wherein the dry eye disease is evaporative dry eye disease.

20. The method of claim 16, wherein the patient is non-responsive, or insufficiently responsive to treatment with aqueous ophthalmic eye drop compositions.

21. The method of claim 16, wherein the patient has a history of dry eye disease in one or both eyes for at least six months.

22. The method of claim 16, wherein the patient has at least one eye, or both eyes with
an inferior corneal fluorescein staining (NEI scale) score of 2 or higher.

* * * * *

UNITED STATES PATENT AND TRADEMARK OFFICE
CERTIFICATE OF CORRECTION

PATENT NO. : 11,413,323 B2
APPLICATION NO. : 17/228309
DATED : August 16, 2022
INVENTOR(S) : Chiara Silvana Leo et al.

It is certified that error appears in the above-identified patent and that said Letters Patent is hereby corrected as shown below:

In the Specification

Column 3, Line 7-8, -with a grades improvement- should be changed to --with a $\geq 3$ grades improvement--

Column 3, Line 12-13, -with a 1 grade improvement- should be changed to --with a $\geq 1$ grade improvement--

Column 13, Line 53, -of 2 according to- should be changed to --of $\geq 2$ according to--

Column 13, Line 55, -of 10- should be changed to --of $\geq 10$--

Column 18, Line 50, -of 2 according to- should be changed to --of $\geq 2$ according to--

Column 18, Line 52, -of 10- should be changed to --of $\geq 10$--

Signed and Sealed this
Twenty-third Day of May, 2023

Katherine Kelly Vidal
*Director of the United States Patent and Trademark Office*